US009230062B2

(12) United States Patent
Seriani

(10) Patent No.: US 9,230,062 B2
(45) Date of Patent: Jan. 5, 2016

(54) SYSTEMS AND METHODS FOR ENABLING CUSTOMERS TO OBTAIN VISION AND EYE HEALTH EXAMINATIONS

(71) Applicant: 20/20 Vision Center LLC, West Palm Beach, FL (US)

(72) Inventor: Joseph S Seriani, Royal Palm Beach, FL (US)

(73) Assignee: 20/20 Vision Center, LLC, Garden City, NY (US)

( * ) Notice: Subject to any disclaimer, the term of this patent is extended or adjusted under 35 U.S.C. 154(b) by 0 days.

(21) Appl. No.: 14/073,812

(22) Filed: Nov. 6, 2013

(65) Prior Publication Data

US 2014/0129259 A1   May 8, 2014

Related U.S. Application Data

(63) Continuation-in-part of application No. PCT/US2013/038508, filed on Apr. 26, 2013.

(60) Provisional application No. 61/723,188, filed on Nov. 6, 2012.

(51) Int. Cl.
*A61B 3/103* (2006.01)
*A61B 3/12* (2006.01)
(Continued)

(52) U.S. Cl.
CPC ........ *G06F 19/3418* (2013.01); *G06F 19/3425* (2013.01)

(58) Field of Classification Search
CPC ............ A61B 5/00; A61B 3/14; A61B 3/103; A61B 3/12; G06Q 10/10; G06Q 50/00; G06Q 60/22; G06Q 50/24
USPC .......................................................... 705/2–4
See application file for complete search history.

(56) References Cited

U.S. PATENT DOCUMENTS 5,280,570 A   1/1994   Jordan
5,515,268 A   5/1996   Yoda
(Continued)

FOREIGN PATENT DOCUMENTS

EP   1062907   12/2000
JP   01-293841   11/1989
(Continued)

OTHER PUBLICATIONS

Ng, ManCho et al. Improviing Access to Eye Care: Teleophthalmology in Alberta, Canada. Journal of Diabetes Science and Technology. vol. 3, Issue 2, Mar. 2009, pp. 289-296.*

(Continued)

*Primary Examiner* — Robert Sorey
*Assistant Examiner* — Kristine Rapillo
(74) *Attorney, Agent, or Firm* — Bryan Cave LLP

(57) ABSTRACT

Systems and methods are provided for eye health and vision examinations. A customer diagnostic center is configured to generate customer examination data pertaining to an examination of a customer's eye. The customer diagnostic center provides a user interface for communicating with a customer and ophthalmic equipment for administering tests to the customer. A diagnostic center server is configured to receive the customer examination data from the customer diagnostic center over a network and allow the customer examination data to be accessed by an eye-care practitioner. A practitioner device associated with the eye-care practitioner is configured to receive the customer examination data from the diagnostic center server and display at least a portion of the customer examination data to the eye-care practitioner. Customer evaluation data is generated pertaining to the eye-care practitioner's evaluation of the customer examination data. An eye health report is provided to the customer via the network.

32 Claims, 10 Drawing Sheets

(51) Int. Cl.
  *G06Q 50/22* (2012.01)
  *G06Q 50/24* (2012.01)
  *G06F 19/00* (2011.01)

(56) References Cited

U.S. PATENT DOCUMENTS

| | | | |
|---|---|---|---|
| 5,592,248 A | 1/1997 | Norton | |
| 5,914,772 A | 6/1999 | Dyer | |
| 5,956,121 A | 9/1999 | Hosoi et al. | |
| 5,983,201 A | 11/1999 | Fay | |
| 6,027,217 A | 2/2000 | McClure et al. | |
| 6,033,076 A | 3/2000 | Braeuning et al. | |
| 6,095,650 A | 8/2000 | Gao et al. | |
| 6,234,978 B1 | 5/2001 | Mihashi et al. | |
| 6,345,260 B1* | 2/2002 | Cummings et al. | 705/7.19 |
| 6,386,707 B1 | 5/2002 | Pellicano | |
| 6,450,643 B1 | 9/2002 | Wilson | |
| 6,499,843 B1 | 12/2002 | Cox et al. | |
| 6,692,127 B2 | 2/2004 | Abitbol et al. | |
| 6,711,460 B1 | 3/2004 | Reese | |
| 6,722,767 B2 | 4/2004 | Dick et al. | |
| 6,761,453 B2 | 7/2004 | Wilson | |
| 6,808,266 B2 | 10/2004 | Youseffi | |
| 7,029,119 B2 | 4/2006 | Youseffi et al. | |
| 7,114,808 B2 | 10/2006 | Lai et al. | |
| 7,128,416 B2 | 10/2006 | Campbell | |
| 7,128,417 B2 | 10/2006 | Isogai | |
| 7,222,091 B2* | 5/2007 | Yoshida | 705/26.8 |
| 7,232,220 B2 | 6/2007 | Franz et al. | |
| 7,267,439 B2 | 9/2007 | Toshima et al. | |
| 7,350,921 B2 | 4/2008 | Ridings | |
| 7,374,285 B2 | 5/2008 | Toshima et al. | |
| 7,384,146 B2* | 6/2008 | Covannon et al. | 351/223 |
| 7,520,611 B2* | 4/2009 | Franz et al. | 351/205 |
| 7,614,747 B2 | 11/2009 | Foster | |
| 7,630,788 B1 | 12/2009 | Reese | |
| 7,840,418 B2* | 11/2010 | Schoenberg | 705/2 |
| 7,874,676 B2 | 1/2011 | Hosoi | |
| 7,883,211 B2 | 2/2011 | Hosoi et al. | |
| 7,891,813 B2 | 2/2011 | Ogilvie | |
| 8,079,707 B2 | 12/2011 | Cabeza et al. | |
| 8,182,091 B2 | 5/2012 | Foster | |
| 2002/0021411 A1 | 2/2002 | Wilson | |
| 2002/0038227 A1 | 3/2002 | Fey et al. | |
| 2003/0117580 A1 | 6/2003 | Franz et al. | |
| 2006/0026051 A1* | 2/2006 | Rose | 705/8 |
| 2007/0203813 A1 | 8/2007 | DiRienzo | |
| 2008/0198328 A1 | 8/2008 | Seriani et al. | |
| 2009/0015787 A1 | 1/2009 | Guillen et al. | |
| 2009/0143652 A1 | 6/2009 | Warburton et al. | |
| 2009/0244485 A1 | 10/2009 | Walsh et al. | |
| 2009/0310084 A1 | 12/2009 | Foster | |
| 2010/0026955 A1 | 2/2010 | Fisher et al. | |
| 2010/0030570 A1 | 2/2010 | Kratzer et al. | |
| 2010/0033678 A1 | 2/2010 | Foster | |
| 2010/0097576 A1 | 4/2010 | Witt et al. | |
| 2010/0293192 A1 | 11/2010 | Suy et al. | |
| 2010/0302509 A1 | 12/2010 | Steinmuller | |
| 2011/0015763 A1 | 1/2011 | Mustonen et al. | |
| 2011/0112927 A1 | 5/2011 | Shimizu | |
| 2011/0194074 A1 | 8/2011 | Spratt | |
| 2011/0273665 A1 | 11/2011 | Saffra | |
| 2012/0016763 A1 | 1/2012 | Kirschner | |
| 2012/0062840 A1 | 3/2012 | Ballou, Jr. et al. | |
| 2013/0141694 A1 | 6/2013 | Seriani | |
| 2014/0028973 A1 | 1/2014 | Scolaro | |

FOREIGN PATENT DOCUMENTS

| | | |
|---|---|---|
| JP | 02-252437 | 10/1990 |
| JP | 10-305013 | 11/1998 |
| WO | WO 02/15818 | 2/2002 |
| WO | WO 03/073922 | 9/2003 |
| WO | WO 2010/117386 | 10/2010 |

OTHER PUBLICATIONS

Comprehensive Adult Eye and Vision Examination, *Optometric Clinical Practice Guideline*, American Optometric Association, Reference Guide for Clinicians, Second Edition 2005.

Eyelogic signs Agreement with 20/20 Vision Center, LLC for USA distribution rights, Canada NewsWire [Ottawa] Sep. 4, 2012.

* cited by examiner

SYSTEMS AND METHODS FOR ENABLING CUSTOMERS TO OBTAIN VISION AND EYE HEALTH EXAMINATIONS

CROSS-REFERENCE TO RELATED APPLICATIONS

The present application claims priority to U.S. Provisional Patent Application No. 61/723,188 filed on Nov. 6, 2012. The present application is also a continuation-in-part of International Application No. PCT/US2013/38508. Both of these applications are incorporated by reference in their entirety.

FIELD OF THE INVENTION

The present invention generally relates to the fields of optometry and ophthalmology and the performance of eye examinations. More specifically, certain embodiments are directed to systems and methods for enabling customers and other users to obtain eye health examinations and vision examinations through a customer diagnostic center that includes ophthalmic equipment and instruments for performing various tests and procedures pertaining to the customers' eye health and visual ability. According to certain of these embodiments, the customer diagnostic center provides data pertaining to the customer and the tests to a remote practitioner via a network for review and evaluation and receives an eye health report from the remote practitioner to be provided to the customer.

BACKGROUND OF THE INVENTION

In today's age of increased awareness of health monitoring and the importance of early detection and prevention of various medical conditions, disorders and diseases, individuals are often required to make visits to medical practitioners for a range of tests and check-ups. For example, it is generally recommended that individuals make regular visits (e.g., once every year, two years, etc.) to practitioners in connection with the monitoring, diagnosis, and treatment of medical conditions in number of areas, such as checking heart-health, detecting various cancers, and monitoring for certain genetically predisposed disorders.

One area in which there is a particular need for regular visits to a medical professional is in connection with the examination of an individual's eyes. Typically, the examination of a person's eyes involves the performance of one or more tests for monitoring and diagnosing eye health, such as detecting glaucoma and retinal disorders, inspecting the pupil, and measuring corneal sensitivity, and/or tests for evaluating visual ability and acuity, such as determining refractive error and detecting color blindness.

There are a number of important benefits to obtaining eye health examinations and/or vision examinations on a regular and continual basis. For example, as with many other types of medical examinations, regular visits and checkups by an individual enable practitioners to monitor and track the health of the individual's eyes and to detect and diagnose certain disorders, diseases and other changes in the patient's eyes and/or vision. Significantly, this allows for early detection, diagnosis and treatment of many conditions, which, in turn, frequently increases the likelihood that the treatment will be successful. In fact, many disorders and diseases are generally treatable or even preventable when detected and diagnosed in the early stages. Also, it is well known that changes in vision can often occur somewhat suddenly, such as at certain periods in a person's life, and eyesight can deteriorate continually over time. Accordingly, another important benefit to regular eye examinations is that they help to ensure that optical prescriptions for individuals are up to date and as accurate as possible.

Given these and numerous other benefits associated with regular eye examinations, it is not surprising that many well-known optometric and ophthalmologic associations and organizations typically recommend that individuals visit eye care professionals once every one or two years Moreover, the need to receive regular eye examinations is particularly important for certain individuals, including those who have a higher likelihood of suffering from various disorders and diseases based on their demographics or other characteristics, such as age, race, profession, individual and/or family history of diseases or disorders, etc. As a result, it is often recommended that many such individuals receive eye exams at least once a year or on an even more frequent basis.

Additionally, it is well known and widely accepted in the eye care and vision field that, in order to maximize these benefits, the regular examinations received by individuals may be in the form of comprehensive eye examinations. Typically, to be considered comprehensive, such examinations may include certain approved tests and procedures and/or meet certain minimum standards and requirements for testing and diagnosis. In particular, comprehensive eye examinations may include some or all of the following tests and procedures (or tests and procedures of an equivalent nature): (i) objective and subjective refraction and/or other tests to check visual acuity; (ii) examination of the extraocular muscles; (iii) peripheral vision test (e.g., by checking the visual field by confrontation); (iv) examination of the external eye; (v) examination of the pupils; (vi) color vision test; (vii) test for stereopsis for depth perception; (viii) evaluation of central vision field (e.g., using the Amsler grid); (ix) cover test for strabismus; (x) an optical coherency tomography (OCT) scan and/or slit lamp examination using biomicroscopy; (xi) examination of eyelids, conjunctiva, cornea, anterior chamber, iris and lens; (xii) measure eye pressure and/or intraocular pressure; (xiii) imaging of fundus using a retinal camera and examination of macula, vessels, optic nerve, peripheral retina, and vitreous humour. In certain cases, it may also be useful to administer particular types of screenings to individuals for certain diseases or disorders (e.g., glaucoma, macular degeneration or hypertensive retina), such as where there is individual and/or family history of diseases or disorders.

Despite the known importance of regular eye health checkups and vision examinations, many individuals only visit eye care professionals and receive eye examinations on a highly sporadic basis. Other individuals fail to visit an eye care professional at all, or only do so in response to suffering from a medical condition or recognizing a potential problem with their vision. In fact, it is estimated that the average American adult receives an eye examination once every five years or more. Likewise, it is estimated that a large percentage of the individuals in America who require some form of vision correction have the wrong correction or no correction. Moreover, even among the individuals that undergo eye exams on a more frequent basis, the examinations received by these individuals often fail to rise to the level of a comprehensive eye examination. For example, when visiting an eye care professional many individuals may simply receive a vision screening and/or a minimal set of visual acuity tests.

While there are various contributing factors, primary reasons why many individuals fail to regularly undergo eye examinations are based on time, cost, and convenience. Typically, in order to obtain an eye examination, an individual required to expend time and effort to seek out, select and make an appointment with an appropriate eye care professional. In turn, time is spent traveling to and from the practitioner's office, waiting for the practitioner, partaking in discussions with the practitioner and/or nurse or assistant and undergoing the examination. Similarly, from the practitioner's perspective, the number of patients that can be seen and examined are limited by a number of factors, such as the time required to examine each patient, update the patient's records, and prepare equipment. As a result, individuals are frequently forced to visit eye care professionals at inconvenient times and/or travel to other, less conveniently located professionals. Also, in order to maximize the number of patients that can be seen, practitioners may limit the number of tests and procedures and/or the time spent on such tests, thereby reducing the time needed for each patient.

Additionally, the costs associated with visiting a practitioner can dissuade, and even prohibit, many individuals from receiving eye examinations on a regular basis. This can be further compounded by the fact that many individuals lack insurance coverage for such examinations and are required to pay some or all of the costs out of pocket. Thus, making regular visits to an eye care professional can often be a time-consuming, inconvenient and expensive commitment. Accordingly, there is a need for novel approaches to providing eye health examinations and vision examinations that minimize the time and cost required by individuals, and thereby encourage individuals to obtain regular examinations.

There have been some attempts in the past to provide systems that simplify and automate the vision testing and examination process. These prior art systems, however, have exhibited a number of drawbacks and limitations, which have resulted in their failure to be adopted by consumers in any meaningful way. One such drawback is that many of these systems only provide vision screening or visual acuity testing. Similarly, many of these systems are limited to a restricted or incomplete set of procedures and tests and do not allow individuals to obtain a comprehensive eye examination. Another drawback is that many of these systems require an on-site eye care practitioner and/or operator to provide some or all of the examination. Other such systems do not allow for any input or feedback from an eye care practitioner. Yet another drawback is that none of these systems provide a real-time interface between the examinee and a remote practitioner. Still yet another drawback is that many of these systems do not include any functionality for automatically detecting or diagnosing potential disorders, defects or risk factors based on an individual's examination data and/or for automatically generating recommendations and/or referrals.

There is, therefore, a need for an eye testing and evaluation system for providing eye health examinations and vision examinations to individuals. There is also a need for a system that allows individuals to obtain eye health examinations and vision examinations through a user-friendly customer diagnostic center that includes a wide range of ophthalmologic and vision testing equipment. There is further a need for a system which enables individuals to receive a comprehensive eye examination. There is further a need for a system having an automated or semi-automated customer diagnostic center that allows individuals to obtain eye health examinations and vision examinations with little or no on-site assistance.

There is also a need for a system that provides an interface between the customer diagnostic center and a remote eye care practitioner over a network. to enable the practitioner to evaluate an individuals eye health and vision. There is further a need for a system that enables the remote practitioner to evaluate an individuals eye health and vision and provides the individual with eye health reports, prescriptions, diagnoses, and/or recommendations from the remote practitioner. There is still further a need for a system that allows a remote practitioner or offsite technician to control or monitor the ophthalmologic and vision testing equipment and/or the administration of various eye health and vision tests to individuals. There is still further a need for a system that can be accessed by individuals at a wide range of convenient locations. There is still further a need for a system that encourages individuals to obtain eye health examinations and vision examinations on a regular basis by reducing the time and cost required.

SUMMARY OF THE INVENTION

In accordance with the certain embodiments, a system is provided that includes a customer diagnostic center that is configured to generate customer examination data pertaining to an examination of a customer's eye and vision. The customer diagnostic center provides a user interface for receiving input and providing information to a customer. The customer diagnostic center also includes ophthalmic equipment for administering tests to the customer and an equipment controller configured to control the operation of the ophthalmic equipment. A diagnostic center server is configured to receive the customer examination data from the customer diagnostic center over a network and allow the customer examination data to be accessed by an eye-care practitioner. A practitioner device associated with the eye-care practitioner is configured to receive at least a portion of the customer examination data from the diagnostic center server and display the received customer examination data to the eye-care practitioner. Customer evaluation data is generated pertaining to the eye-care practitioner's review and evaluation of the customer examination data. An eye health report is provided to the customer via the network.

In accordance with certain embodiments, a method is provided for eye health and vision examinations. The method includes generating customer examination data pertaining to an examination of a customer's eye at a customer diagnostic center. The customer diagnostic center includes a user interface for receiving input from, and providing information to, the customer. The customer diagnostic center also includes ophthalmic equipment for administering tests to the customer and an equipment controller configured to control the operation of the ophthalmic equipment. Customer examination data is received from the customer diagnostic center over a computer network at a diagnostic center server. The diagnostic center server permits the customer examination data to be accessed by an eye-care practitioner. The customer examination data is received at a practitioner device associated with the eye-care practitioner from the diagnostic center server. At least a portion of the customer examination data is displayed to the eye-care practitioner. Customer evaluation data pertaining to the eye-care practitioner's review and evaluation of the customer examination data is generated. An eye health report based, at least in part, on the customer evaluation data is provided to the customer via the network.

In accordance with certain embodiments, a server is configured to provide services associated with eye health and vision examinations. The server is configured to receive customer examination data over a computer network pertaining to an examination of a customer's eye administered at a customer diagnostic center. The customer diagnostic center includes a user interface for receiving input from, and providing information to, the customer. The customer diagnostic center also includes ophthalmic equipment for administering tests to the customer and an equipment controller configured to control the operation of the ophthalmic equipment. The server is configured to provide access to the customer examination data by an eye-care practitioner and to transmit the customer examination data from the diagnostic center server to a practitioner device associated with the eye-care practitioner. The server is further configured to receive customer evaluation data pertaining to the eye-care practitioner's review and evaluation of the customer examination data. An eye health report based, at least in part, on the customer evaluation data is provided to the customer via the network.

In accordance with certain embodiments, a system is configured to provide eye health and vision examinations. The system includes a plurality of diagnostic centers which are configured to transmit requests over a network for selecting eye-care practitioners to administer eye examinations for customers and to receive instructions over the network to remotely control operation of ophthalmic equipment in order to administer one or more tests pertaining to the eye examinations. The diagnostic centers are also configured to generate customer examination data pertaining to the one or more tests administered using the ophthalmic equipment. The system also includes a plurality of practitioner devices associated with eye-care practitioners which are configured to receive and display at least a portion of the customer examination data in response to accepting one or more of the requests and to generate customer evaluation data associated with the one or more accepted requests. The system further includes at least one server. In response to receiving the requests from the diagnostic centers, the server analyzes practitioner data to select eye-care practitioners for handling the requests. The practitioner data may comprise availability data indicating whether the eye-care practitioners are currently connected to the system and available to administer eye examinations, scheduling data indicating days and hours that the eye-care practitioners are available to handle the requests and prior customer data that identifies customers who utilized the eye-care practitioners for prior eye examinations. The server is configured to receive the customer examination data from the diagnostic centers and to transmit the customer examination data to the practitioner devices associated with the selected eye-care practitioners. The server is further configured to receive customer evaluation data from the practitioner devices associated with the selected eye-care practitioners. Eye health reports based, at least in part, on the selected eye-care practitioners' review and evaluation of the customer examination data are provided to the customers.

In accordance with certain embodiments, a server is configured to provide services related to eye health and vision examinations. A request is received by the server over a network from a diagnostic center for selecting an eye-care practitioner to administer an eye examination to a customer. In response to receiving the request, the server analyzes practitioner data to select the eye-care practitioner for handling the request. The practitioner data includes availability data indicating which eye-care practitioners are currently available to administer the eye examination, scheduling data indicating days and hours that eye-care practitioners are available to handle requests and prior customer data that identifies one or more eye-care practitioners who previously administered eye examinations to the customer. The server is further configured to receive customer examination data generated by ophthalmic equipment at the diagnostic center while administering one or more tests pertaining to the eye examination and to transmit customer examination data pertaining to the one or more tests to the practitioner device associated with the selected eye-care practitioner. Customer evaluation data is received from the practitioner device associated with the selected eye-care practitioner. An eye health report based, at least in part, on the selected eye-care practitioner's review and evaluation of the customer examination data is provided to the customer.

These and other features and advantages will become apparent from the following detailed description of illustrative embodiments thereof, which is to be read in connection with the accompanying drawings.

BRIEF DESCRIPTION OF THE DRAWINGS

The inventive principles are illustrated in the figures of the accompanying drawings which are meant to be exemplary and not limiting, in which like references are intended to refer to like or corresponding parts, and in which.

DETAILED DESCRIPTION OF EMBODIMENTS OF THE INVENTION

Figure 1:
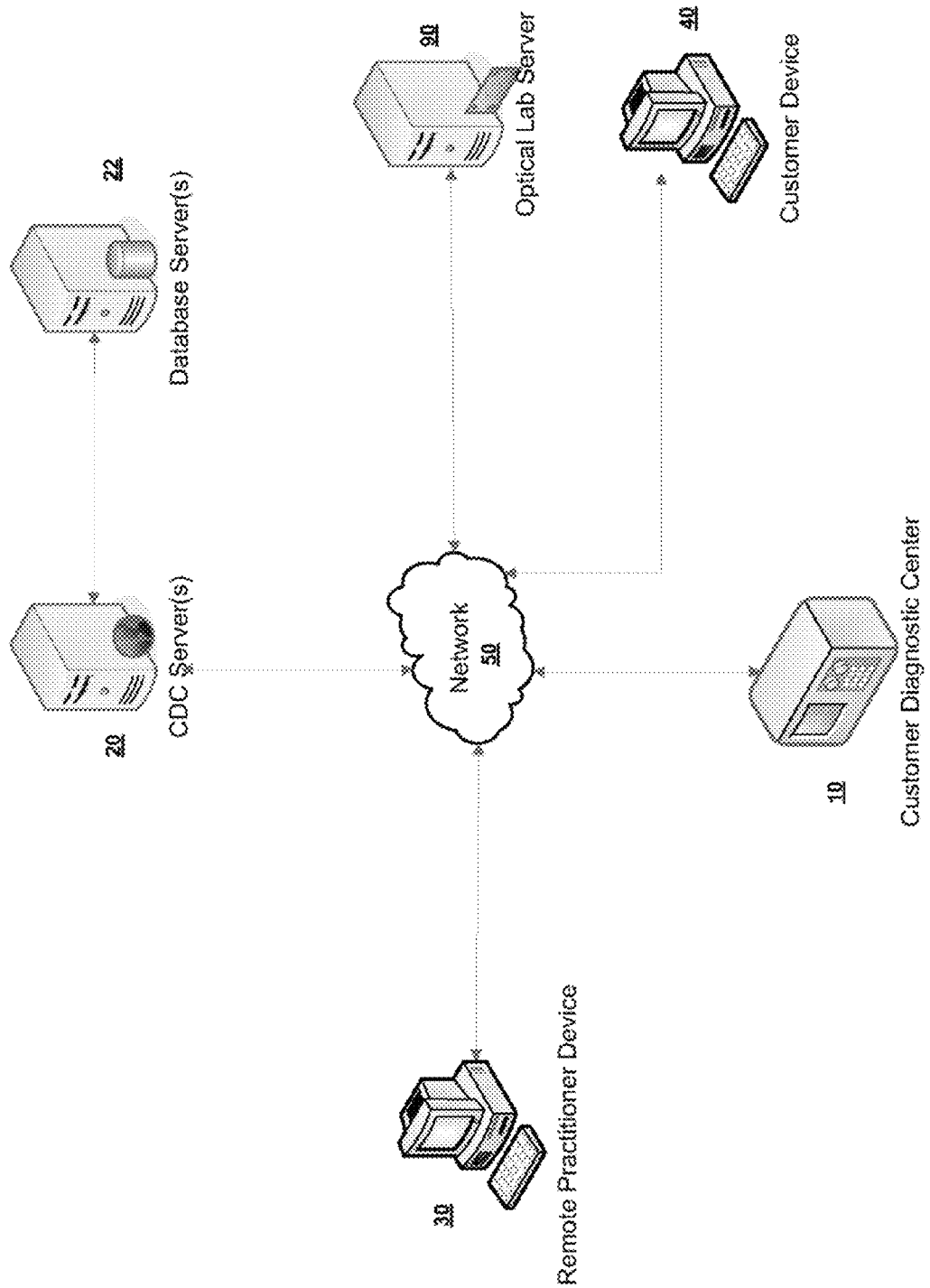
FIG. 1 is a pictorial diagram of an eye testing and evaluation system in accordance with certain embodiments of the present invention.

In the following description, reference is made to the accompanying drawings that form a part hereof, and in which is shown by way of illustration specific embodiments in which the invention may be practiced. It is to be understood that other embodiments may be utilized and structural changes may be made without departing from the scope of the present invention.

It is well-known that eye health examinations and vision examinations provide many important benefits and, accordingly, virtually all highly-regarded associations and professionals throughout the field of eye and vision care strongly recommend that individuals receive such examinations and screenings on a regular and consistent basis. Nevertheless, many individuals fail to undergo eye health examinations and vision examinations at all, or only do sporadically or in response to an immediate medical issue or condition. In part, many individuals find it challenging to obtain regular examinations because of the significant time, cost and inconvenience that can be required in connection with finding an eye care professional, making an appointment and visiting the professional's office to receive the examination. To encourage regular eye health examinations and vision examinations by such individuals and others, systems and methods are provided herein that allow individuals to obtain eye health examinations and vision examinations through customer diagnostic centers at a wide range of convenient locations, thereby reducing the time and expense incurred by such individuals.

Certain embodiments of the present invention pertain to an eye testing and evaluation system, including devices, general hardware components and computer hardware and software for providing eye health examinations and/or vision examinations to customers (i.e., any individual desiring eye health examinations and/or vision examinations). According to certain of these embodiments, the customers may receive the eye health examinations and/or vision examinations at a customer diagnostic center that includes various ophthalmologic and/or vision testing equipment and instruments for administering a range of tests and procedures and collecting various data pertaining to the customers' eyes and vision. In certain embodiments, the customer diagnostic center interfaces with a remote practitioner (e.g., ophthalmologist, optometrist, or other suitable eye doctor or eye care professional) through a network. According to certain of these embodiments, various data, including data pertaining to a customer and data associated with the eye health and vision tests and procedures administered to the customer is provided to the remote practitioner for analysis, diagnosis and/or confirmation. In certain embodiments, an eye health report, optical prescription, recommendations and/or referrals based on the customer and testing data are received from the remote practitioner and provided to the customer. Certain embodiments enable the ophthalmologic and/or vision testing equipment in the customer diagnostic center and/or the administration of various tests and procedures to be controlled or monitored by the remote practitioner or an off-site technician via a remote equipment interface.

The eye testing and evaluation system, corresponding arrangements and systems, apparatuses, and methods described below address many of the hurdles and restrictions that currently exist with respect to administering eye health examinations and vision examinations to individuals and encourages individuals to undergo such examinations and examinations on a regular and consistent basis by providing customer diagnostic centers at various convenient locations that allow individuals to obtain eye health examinations and vision examinations with little or no assistance, thereby minimizing the time, effort, and cost involved.

Eye Testing and Evaluation System Architecture

Figure 2:
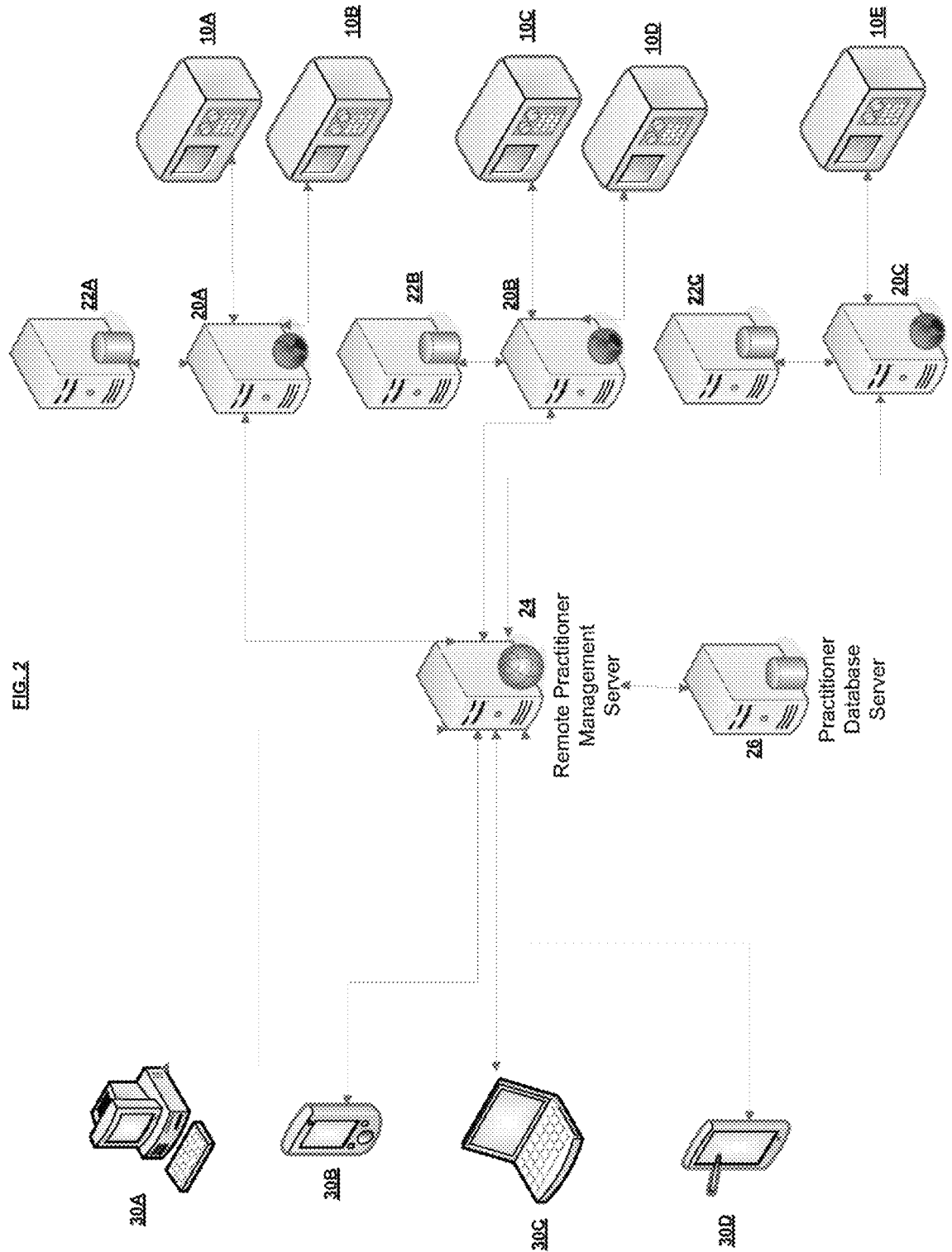
FIG. 2 is a pictorial diagram of an eye testing and evaluation system in accordance with certain embodiments of the present invention.

In certain embodiments, the eye testing and evaluation system may be provided through any suitable form of general hardware components and devices, computer hardware and software, or a combination of any of the foregoing, that allows customers to obtain eye health examinations and/or vision examinations. The eye health examinations and/or vision examinations may include comprehensive examinations and/or screenings. Exemplary illustrations of the architecture of the eye testing and evaluation system and accompanying apparatuses, systems and components, in accordance with certain embodiments, are shown in FIGS. 1-2 and described below. As shown in FIGS. 1-2, the system may include various components and subcomponents, such as apparatuses, equipment, servers, processors, networks, and personal devices which are part of the eye testing and evaluation system.

It is to be understood that the components depicted may be logical components and that the terminology used herein to describe each component is for illustrative purposes and is not to be construed as limiting. Each component and subcomponent may include the necessary apparatuses, devices and computer hardware, software and firmware to enable the collecting, measuring, processing, storing, communicating, presenting and/or receiving of data. A component or subcomponent may include one or more electronic components, mechanical components, instruments, computer processors, computer servers, data stores, storage mediums, memory, etc. The functionality of a component may be directed by one or more executable computer-readable instructions received via a computer-readable storage medium. A processor may be included to execute one or more functions per instructions, programs, or processes stored in the processor itself and/or stored in another memory source. Memory may be any mechanism that is capable of storing data, such as computer programs, instructions, and other necessary data. One or more interfaces may be included to enable the presentation, manipulation, transmission, and receipt of data. Communication of data may be enabled by one or more networks or physical connections. Any data transmitted by or between components may be encrypted for security purposes (e.g., with a 256-bit advanced encryption algorithm). A network may include one or more wide-area networks (WAN) (such as the Internet), local area networks (LAN), wireless local area networks (WLAN), a mobile wireless network, a combination of any of the foregoing, and/or any other suitable networks and may include any component (physical or logical) necessary for utilizing a particular network's functionality, such as routers, adapters, subnets, etc.

FIG. 1 is a pictorial diagram of an eye testing and evaluation system 100 in accordance with certain embodiments. As shown in FIG. 1, the system includes customer diagnostic center 10 having various components, such as general hardware components, mechanical devices, electronic equipment, computer hardware and software and other suitable components for allowing customers to receive eye health examinations and/or vision examinations. In certain embodiments, customer diagnostic center 10 includes various ophthalmic equipment and instruments, such as refractors, lensometers, tonometers, biomicroscopes, etc., for administering a range of tests and procedures to customers. In certain embodiments, customer diagnostic center 10 includes one or more interfaces, such as a customer interface for receiving inputs, selections, responses and other data from customers and outputting various information to the customers. Customer diagnostic center 10 may also include a network interface for communicating with various other systems and devices over one or more networks, such as network 50 shown in FIG. 1. In certain embodiments, customer diagnostic center 10 may include an operator interface for allowing an onsite technician or operator to monitor or control the ophthalmic equipment and instruments (or a portion thereof) and/or the administration of tests and procedures to customers.

According to certain embodiments, customer diagnostic center 10 may include computer hardware, software, or a combination thereof, such as processors, memory, controllers, applications, and other suitable computing devices and components that control the overall operation of customer diagnostic center 10. For example, these components may facilitate the administration of eye health examinations and vision examinations, process data received from customers and operators and data generated by the ophthalmic equipment and instruments, and/or manage the communication of data to and from other systems and devices over a network. The devices, equipment, computer hardware and software and other components that may be included within and/or utilized by customer diagnostic center 10 are further illustrated and described below in connection with FIGS. 3-5.

In certain embodiments, customer diagnostic center 10 may be provided in the form of a self-contained structure, such as a booth or other suitable enclosure. In certain of these embodiments a number of structures may be provided, each of which may include certain components of customer diagnostic center 10. In certain of these embodiments, customer diagnostic center 10 may be of sufficient size to allow customers to enter and/or sit down therein. According to certain other embodiments, customer diagnostic center 10 (or a portion thereof) may be provided in a free-standing form, such as a kiosk, terminal, or the like, or may be incorporated within one or more existing structures, such as eyeglass or contact lens dispensing machines or other types of devices associated with viewing, trying-on (e.g., physically or virtually), customizing, ordering and/or purchasing eyeglasses and contact lenses. According to yet other embodiments customer diagnostic center 10 may be provided in any structure or form that is suitable for housing the various components described herein and allowing customers to receive eye-health examinations and vision examinations.

Customer diagnostic center 10 may be provided in a wide range of locations and environments. For example, in certain embodiments, customer diagnostic center 10 may be provided at various shopping locations, such a retail store, malls, event centers, office buildings, or other indoor spaces. In certain of these embodiments, customer diagnostic center 10 may be located within a retail store, office or the like that is associated with providing one or more eye care and/or vision products or services, such as an eye clinic, prescription lens lab or store, or optician's, optometrist's or ophthalmologist's office. As another example, customer diagnostic center 10 may be provided at various outdoor locations and environments, such as strip malls, outlet malls, or town centers. In certain embodiments, er diagnostic center 10 may be provided at the home or residence of a customer or individual seeking an examination. In certain other embodiments, customer diagnostic center 10 may be provided at virtually any location or environment that is suitable for allowing customers to access customer diagnostic center 10 and receive eye-health examinations and vision examinations. In certain embodiments, customer diagnostic center 10 may be provided as a fixed structure or device or may be designed to be portable or mobile.

As illustrated in FIG. 1, the eye testing and evaluation system may include customer diagnostic center server (CDC server) 20, which may be in the form of computer hardware, software, or a combination thereof, including any number of physical or virtual computer servers, or any other suitable computing device or devices. In certain embodiments, CDC server 20 and/or database server 10 may be hosted and operated by the owner or operator of customer diagnostic center 10. In certain other embodiments, CDC server 20 and/or database server 10 may be hosted and operated by one or more third-party service providers. According to certain of these embodiments, customer diagnostic center 10 and CDC server 20 may communicate with each other through network 50, which may be any suitable type of wired and/or wireless network. such as an Internet network.

In certain embodiments, CDC server 20 may provide various services and functionality required by, and/or manage or control certain functionality associated with, customer diagnostic center 10. For example, in certain embodiments, CDC server 20 may be responsible for storing, maintaining, updating, processing and/or providing access to, various data received from or used by customer diagnostic center 10, such as data pertaining to customers, examination results data associated with tests and procedures administered through the customer diagnostic center 10, and/or practitioner evaluation data pertaining to a remote practitioners review, diagnoses, and evaluation of the examination results data. In certain embodiments, CDC server 20 may store video recordings of examinations and tests performed at customer diagnostic center 10 and permit practitioners to access the recordings remotely. In certain embodiments, CDC server 20 may store introductory videos and/or advertisements that are transmitted to customer diagnostic center 10 and displayed to customers at customer diagnostic center 10 prior to administering tests and/or procedures to the customer. CDC server 20 may also store, maintain and/or provide access to data received from or associated with other sources, such as medical history data and prior examination data for customers, testing data pertaining to the tests and procedures available through customer diagnostic center 10 and/or product data, promotional data and advertising data associated with eye care and vision related products and services provided by various third parties. In certain of these embodiments, CDC server 20 may also utilize one or more database servers, such as database server 22 shown in FIG. 1, to facilitate the storage, organization, and retrieval of some or all of the data maintained by CDC server 20 in one or more databases maintained by database server 22. CDC server 20 may access database server 22 through any suitable connection, such as a physical connection, local network, and/or network 50.

As another example, CDC server 20 may be responsible for managing, controlling, and/or updating certain functionality associated with customer diagnostic center 10. In certain embodiments, CDC server 20 may store various software, programs, instructions, testing data and other information that is used by customer diagnostic center 10 in connection with enabling customers to access and obtain eye health examinations and vision examinations, controlling the ophthalmic equipment and instruments, and/or providing and administering tests and procedures to customers. As yet another example, CDC server 20 may be responsible for managing and facilitating the establishment of connections and/or communication of data between customer diagnostic center 10 and various other systems and devices over one or more networks, such as devices associated with a remote eye care practitioner or offsite technician, devices associated with customers, and/or systems associated with third party providers of eye care and vision products and services.

Although CDC server 20 and database server 22 are shown in FIG. 1 for illustrative purposes, it should be understood that in certain embodiments the functionality provided by CDC server 20 and/or database server 22, may be provided by any number of servers, or other suitable computing hardware, software and/or devices. Alternatively, or additionally, some or all of the functionality provided by CDC server 20 and/or database server 22 may be integrated with customer diagnostic center 10. In certain other embodiments, CDC server 20 and/or database server 22 may be directly connected to customer diagnostic center 10.

In certain embodiments, customer diagnostic center 10 and/or CDC server 20 may interface with a remote eye care practitioner through one or more devices associated with the practitioner, such as remote practitioner device 30 shown in FIG. 1. Remote practitioner device 30 may be a computing device, such as a personal computer, workstation, laptop, tablet, smartphone, or PDA, or any other suitable device of that enables a remote practitioner to receive, access, view, and/or send data over one or more networks (e.g., network 50). In certain embodiments, the remote eye care practitioner may be a licensed optometrist or ophthalmologist. In certain other embodiments, the remote eye care practitioner may be any eye care professional or other individual who is qualified, licensed, or otherwise capable of administering or monitoring one or more eye health and visual acuity tests and procedures and/or reviewing, analyzing and providing diagnoses, reports, prescriptions or recommendations based upon the data and results associated with administering such tests and procedures.

According to certain embodiments, various data associated with the eye health examinations and vision examinations administered to the customers through customer diagnostic center 10 may be sent to (or made accessible to) the remote practitioner at remote practitioner device 30. For example, in response to a customer accessing customer diagnostic center 10 and receiving certain eye health and vision tests, customer examination data may be sent to remote practitioner device 30 for review by the remote practitioner. In certain embodiments, the customer examination data may include data pertaining to the customer (e.g., the customer's name, age, gender, race, medical history, prior test results, etc.) and data associated with one or more of the tests administered to the customer (e.g., responses, inputs and selections from the customer, instrument measurements and readings, test results, etc.). In certain embodiments, the customer examination data may include a real-time video stream that permits the remote eye care practitioner to view the patient as tests, procedures and examinations are provided to the customer, or may include a video recording that permits the remote eye care practitioner to view tests, procedures and examinations that were previously administered to the customer. In certain of these embodiments the customer examination data may also include various other data that enables the remote practitioner to (or assists the remote practitioner with) evaluate the customer's eye health and visual ability, detect and diagnose certain disorders, defects and conditions and/or confirm that one or more of the tests and procedures were administered correctly.

In certain embodiments, customer evaluation data may be received from the remote practitioner via remote practitioner device 30 that is based on the remote practitioner's review and evaluation of the customer examination data. The customer evaluation data received from the remote practitioner may include various reports, diagnoses, recommendations and other information indicating the results of the eye health and vision tests and procedures administered to the customer. For example, in certain of these embodiments the customer evaluation data may include an eye health report (or may be used to generate an eye health report) that may include an overview of the customer's eye health, visual acuity, the results of one or more tests and procedures, diagnoses of one or more eye or vision disorders or conditions, optical prescriptions, pharmaceutical prescriptions, recommendations, treatment instructions, and/or referrals to see other eye care professionals. In certain embodiments, the eye health report and/or customer evaluation data (or a portion thereof) may be provided to the customer, such as by presenting the eye health report to the customer through diagnostic center 10 and/or allowing the customer to access the eye health report from one or more computing devices associated with the customer.

According to certain embodiments, the communication of some or all of the data sent to and received from the remote practitioner (e.g., customer examination data and customer evaluation data) may be managed and facilitated by CDC server 20. For example, in response to a customer receiving an eye health examination and/or vision examination at customer diagnostic center 10, CDC server 20 may store various data (e.g., customer data, testing data, etc.) received from customer diagnostic center 10 and manage the delivery of the corresponding customer examination data to the remote practitioner. In certain of these embodiments, CDC server 20 may send the customer examination data to remote practitioner device 30 through any suitable delivery mechanism, such as e-mail, text message, file transfer, etc. Alternatively, or additionally, the remote practitioner may be able to access, view and/or download the customer examination data from CDC server 20, such as by using remote practitioner device 30 to access the customer examination data through a web-based service or similar network-based application hosted by CDC server 20 and/or a client application installed on remote practitioner device 30 that is adapted to connect to CDC server 20.

In turn, the receipt of various data from the remote practitioner may be managed by CDC server 20 in a similar manner. For example, after receiving and reviewing the customer examination data, the remote practitioner may send the customer evaluation data to CDC server 20. In certain embodiments, such as where the customer examination data may be accessed and viewed through a web-based service or client application, the remote practitioner may also be able to generate and/or provide the customer evaluation data through the web-based service or client application. In certain of these embodiments, the web-based service or client application may assist the remote practitioner with the process of creating the customer evaluation data, such as by providing a graphical user interface or the like that allows the remote practitioner to make selections, input, upload and edit various data, and generate various reports. In certain other embodiments, CDC server 20 may receive the customer evaluation data from the remote practitioner through any suitable delivery mechanism, such as email.

According to certain other embodiments, CDC server 20 may facilitate and/or establish a connection between customer diagnostic center 10 and remote practitioner device 30 in order to allow the direct communication of certain data between customer diagnostic center 10 and remote practitioner device 30. In certain of these embodiments, a real-time connection may be established between customer diagnostic center 10 and remote practitioner device 30, which allows the remote practitioner to view and interact with a customer, access and view customer examination data, and/or provide customer evaluation data to the customer in real-time, such as during (or shortly after) the administration of one or more eye health and vision tests. The remote practitioner may also be able to monitor and control certain ophthalmic equipment and instruments and/or the administration of one or more eye health and vision tests in real-time. As an alternative (or in addition), CDC server 20 may establish a real-time connection between customer diagnostic center 10 and a device associated with an offsite technician (e.g., an equipment operator or the remote practitioner's assistant, etc.) for monitoring and/or controlling the equipment and the administration of the tests. The process of establishing connections with and communicating various data to and from various devices associated with remote practitioners and off-site technicians is described in further detail below.

In certain embodiments, CDC server 20 may also manage the communication of certain data to various other systems and devices. For example, as shown in FIG. 1, in certain embodiments, after receiving an eye health examination and/or vision examination through customer diagnostic center 10, customers may be able to access some or all of the data associated with their examination or examination (e.g., an eye health report) from various devices, such as customer device 40 via network 50. Customer device 40 may be any suitable type of computing device that is associated with the customer, such as a personal computer, laptop, tablet, PDA, smartphone, etc. In certain of these embodiments, the data may be delivered and/or made accessible to customers through a web or network based service provided by CDC server 20 or a client application installed on customer device 40 in a similar manner to that described above in connection with communicating with the remote practitioner. In certain embodiments, customers may also be able to view, input and/or update other information, such as their customer data. Additionally, customers who have not yet received an eye health examination or vision examination through customer diagnostic center 10 may be able to enter certain background information and/or create an account in advance, such as to avoid having to provide this information when visiting customer diagnostic center 10.

As another example, CDC server 20 may forward certain data associated with customers and their eye health examinations and/or vision examinations to a third party provider of eye-care and vision related products and services, such as to an optical lab through optical lab server 90 (as shown in FIG. 1) or to an eye care professional (not shown) through network 50. In certain of these embodiments the data may only be sent to a third party provider in response to receiving a request from the customer. In certain other embodiments, CDC server 20 may be configured to automatically deliver certain data to one or more third party providers, such as in response to receiving customer evaluation data from a remote practitioner that includes a recommendation and/or referral for the customer to visit an eye care professional in-person.

Although the foregoing describes various examples in which CDC server 20 manages, facilitates, and/or controls the communication of certain data to one or more devices and systems (e.g., remote practitioner device 30 and customer device 40), these examples are intended to be illustrative, not limiting. It should be understood that these (and various other) communications could be managed, facilitated, and/or controlled by one or more other devices or components included with the eye testing and examination system, and/or various third-party or external systems, devices and components. For example, in certain embodiments, such as where customer diagnostic center 10 incorporates some or all of the functionality associated with CDC server 20 and/or database server 22, customer diagnostic center 10 may send customer examination data directly to remote practitioner device 30 and/or make the data accessible to remote practitioner device 30 via a web or network based service or through a client software application. Likewise, in certain embodiments, customer diagnostic center 10 may establish a real-time connection with remote practitioner device 30 and/or a device associated with an off-site technician, and may manage the communication of data to and from various other systems and devices, such as customer device 40 and/or optical lab server 90.

FIG. 2 is a pictorial diagram of an eye testing and evaluation system in accordance with certain other embodiments. In certain embodiments, the eye testing and evaluation system may include a number of customer diagnostic centers. For example, as shown in FIG. 2, the eye testing and evaluation system may include customer diagnostic centers 10A-10E. In certain embodiments, customer diagnostic centers 10A-10E may be in a form similar to the customer diagnostic centers illustrated and described in connection with FIGS. 1 and 3-5 (e.g., customer diagnostic center 10). In certain other embodiments, some or all of customer diagnostic centers 10A-10E may include a limited set of components and/or provide a limited set of features and functionality. For example, customer diagnostic centers 10A and 10C may be configured to provide customers with vision examinations, customer diagnostic centers 10B and 10D may be configured to provide customers with eye health examinations and customer diagnostic center 10E may be configured to provide customers with vision examinations and eye health examinations. The vision examinations and eye health examinations may include both comprehensive examinations and screenings (e.g., screenings that may be necessitate referral to a specialist for further evaluation). In yet other embodiments, one or more of the customer diagnostic centers may include additional components and/or provide additional features and functionality, such as functionality related to ordering and purchasing eye care and vision products and services.

In certain embodiments, customer diagnostic centers 10A-10E may all be owned, operated and/or maintained by the same party, such as a third party associated with the manufacture and/or servicing of the customer diagnostic centers or a company associated with the sale of various eye care and vision products and services. For example, customer diagnostic centers 10A-10E may each be provided at a retail store or other physical location that is associated with an optician or prescription lens company. In certain other embodiments, customer diagnostic centers 10A-10E may be owned, operated and/or maintained by a number of different third parties. According to certain preferred embodiments, the customer diagnostic centers may be provided at a wide range of locations and environments (e.g., retail stores, department stores, malls, doctor's offices, etc.), thereby making it as convenient as possible for customers to locate and visit a customer diagnostic center and obtain eye health examinations and vision examinations.

In certain embodiments, customer diagnostic centers 10A-10E may interface with a number of CDC servers over one or more networks (such as network 50 shown in FIG. 1). For example, as shown in FIG. 2, customer diagnostic centers 10A and 10B may interface with CDC server 20A, customer diagnostic centers 10C and 10D may interface with CDC server 20B, and customer diagnostic center 10E may interface with CDC server 20C. In certain of these embodiments, CDC servers 20A-20C may manage or control certain operations of customer diagnostic centers 10A-10E, provide various functionality and resources used by customer diagnostic centers 10A-10E, and/or enable or facilitate certain communications between customer diagnostic centers 10A-10E and various other systems and devices, in a similar manner to that of CDC server 20 described above in connection with FIG. 1. In certain embodiments, CDC servers 20A-20C may be provided in the form of separate physical computer servers, or may be provided in the form of virtual servers running on a one or more physical computer servers. In certain other embodiments, the functionality associated with CDC servers 20A-20C may be incorporated with a single CDC server (e.g., CDC server 20 shown in FIG. 1), which interfaces with customer diagnostic centers 10A-10E.

In certain embodiments, such as illustrated in FIG. 2, each CDC server may interface with a subset of the customer diagnostic centers that are provided through the eye testing and evaluation system. For example, each CDC server may be associated with a particular predefined subset of customer diagnostic centers. As another example, a CDC server may be associated with customer diagnostic centers that are located within a specified geographic region (e.g., a city, state, etc.) and/or customer diagnostic centers that are owned or operated by a particular third party (e.g., a prescription lens retailer). In certain other embodiments, a separate CDC server may be included for each customer diagnostic center that is provided through the eye testing and evaluation system (i.e., a one-to-one relationship). Additionally, while FIG. 2 shows each customer diagnostic center interfacing with a single CDC server, in certain embodiments, customer diagnostic centers 10A-10E may be able to interface with multiple CDC servers.

According to certain embodiments, CDC servers 20A-20C may interface with one or more database servers, such as database servers 22A-22C shown in FIG. 2. For example, CDC servers 20A-20C may utilize database servers 22A-22C, respectively, to store, retrieve, and access various data that is generated by, related to, and/or used by the customer diagnostic centers, such as customer data, testing administration data, customer examination data, and customer evaluation data, in a similar manner to that described in connection with FIG. 1. In certain of these embodiments, each CDC server may utilize a separate database server (or servers) to store the data that is associated with the particular customer diagnostic centers that are managed or controlled by the CDC server. In certain other embodiments, a central database server (or group of database servers) may be provided that is accessed and utilized by some or all of the CDC servers. One benefit to the use of a central database is that it enables data associated with a particular customer diagnostic center to be accessed quickly and efficiently at various other customer diagnostic centers, such as where a customer visits a number of customer diagnostic centers at different times.

In certain embodiments, such as where customer examination data and/or other information is provided to a remote practitioner for review and analysis of a customer's eye health or visual ability, customer diagnostic centers 10A-10E and/or CDC servers 20A-20C may communicate with a number of remote practitioners. For example, customer diagnostic centers 10A-10E and/or CDC servers 20A-20C may communicate with remote practitioners through remote practitioner devices 30A-30D, as shown in FIG. 2. In certain of these embodiments, the remote practitioner devices may include a wide range of computing devices, such as remote practitioner workstation 30A, remote practitioner smartphone 30B, remote practitioner laptop 30C and remote practitioner tablet 30D. Remote practitioner devices 30A-30D may include devices that are associated with a particular remote practitioner (e.g., a personal smartphone, PC, or tablet), devices that are associated with a number of remote practitioners (e.g., a workstation or company laptop) and/or a combination of the foregoing.

In certain of embodiments, customer diagnostic centers 10A-10E and/or CDC servers 20A-20C may communicate with remote practitioner devices 30A-30D over one or more networks using any suitable communications mechanisms and/or protocols, such as those described above in connection with FIG. 1. For example, customer diagnostic centers 10A-10E and/or CDC servers 20A-20C may send data to and/or receive data from remote practitioner devices 30A-30D through one or more standard transfer mechanisms (e.g., e-mail). Alternatively, or in addition, customer diagnostic centers 10A-10E and/or CDC servers 20A-20C may provide data to and receive data from the remote practitioners through a client-server framework, such as a web based service hosted by CDC servers 20A-20C and accessed by remote practitioner devices 30A-30D (e.g., via a web browser) or a client application installed on remote practitioner devices 30A-30D that connects to a server application running on CDC servers 20A-20C.

As illustrated in FIG. 2, some or all of the communications and connections between remote practitioner devices 30A-30D and customer diagnostic centers 10A-10E and/or CDC servers 20A-20C may be facilitated by one or more intermediary servers, such as remote practitioner management (RPM) server 24. In certain embodiments, RPM server 24 may simply act as a central gateway or proxy server that provides various interfaces through which data can be communicated to and received from the remote practitioner devices. In certain other embodiments, RPM server 24 may play a more active role and provide various features and functionality associated with managing, controlling and/or tracking the communications and/or connections with the remote practitioner devices. For example, RPM server 24 may keep track of the remote practitioners and/or remote practitioner devices that are associated with the eye testing and evaluation system and/or manage the distribution of data to the remote practitioners. In certain embodiments, the RPM server 24 may maintain a listing of remote practitioners, remote practitioner devices 30, customer diagnostic centers 10 and any other component or individual that is currently connected to the eye testing and evaluation system. The listing may be utilized to establish a connection between a remote practitioner device 30 and a customer diagnostic center 10.

In certain embodiments, RPM server 24 may utilize one or more database servers, such as practitioner database server 26 shown in FIG. 2, to store and access various data pertaining to the remote practitioners and the remote practitioner devices. Among other things, the practitioner data may include certain background information for each remote practitioner (e.g., name, age, qualifications, location, etc.), data indicating one or more remote practitioner devices associated with each remote practitioner and/or data pertaining to one or more communication mechanisms through which data may be delivered to and/or made accessible to the remote practitioners. In turn, RPM server 24 may access and use the practitioner data (or a portion thereof) in a number of manners.

For example, RPM server 24 may use the practitioner data in connection with forwarding data from the CDC servers and/or customer diagnostic centers to remote practitioners, such as to determine how the data should be delivered (e.g., e-mail, through a client application, etc.) and/or where the data should be delivered (e.g., determine one or more remote practitioner devices). Similarly, the practitioner data may be used to confirm whether data should be delivered to a particular remote practitioner (e.g., whether the remote practitioner is currently providing services through the system, connected to the system or whether the remote practitioner has certain required qualifications or expertise). As another example, RPM server 24 may provide some or all of the practitioner data to the CDC servers and/or customer diagnostic centers, such as to allow a customer to view and/or select from one or more remote practitioners, and/or to enable the CDC servers or customer diagnostic centers to determine remote practitioners to communicate with. In certain of these embodiments, the practitioner data may keep track of the customers for which each remote practitioner has reviewed examination data and/or provided eye health reports, optical prescriptions, etc., thereby allowing RPM server 24 (or the CDC servers or customer diagnostic center) to determine whether the data for a current customer can be sent to a remote practitioner that may already be familiar with the customer (e.g., in the case that the remote practitioner previously examined or interacted with the customer).

In certain embodiments, the practitioner data may store data that pertains to the availability and/or status of each remote practitioner. This data may include, for example, information related to a remote practitioner's schedule, the days and/or hours that a remote practitioner is available to review customer examination data through the system, whether the remote practitioner is on vacation, etc. The availability data may be used in various ways to manage the communication of data to the remote practitioners, such as determining whether a particular remote practitioner is able to review customer examination data, and/or providing a list of the currently available remote practitioners to the CDC servers and/or customer diagnostic centers. In certain of these embodiments, such as where a real-time connection is established between customer diagnostic centers and remote practitioners, the availability data may include an indication of whether each remote practitioner is online and/or available for connecting to a customer diagnostic center (e.g., is not already connected to a customer diagnostic center, has a sufficient network connection, is using a supported remote practitioner device, etc.).

Likewise, the practitioner data may include data that is associated with monitoring and tracking the current workload of the remote practitioners through the system (e.g., the number of customers for which each remote practitioner is in the process of reviewing and analyzing examination data). In turn, this data can be used by RPM server 24 to determine and select the remote practitioners who have availability to review examination data associated with additional customers. Alternatively, or additionally, this tracking data may be used to determine or prioritize the remote practitioners that should be assigned customer examination data as it is received, such as by keeping a list of the remote practitioners that is ordered based on how long it has been since customer examination data was provided to each remote practitioner. Accordingly, by monitoring and tracking the workload of the remote practitioners, RPM server 24 is able to distribute the customer examination data to the pool of remote practitioners in a balanced manner, thereby minimizing the amount of time each customer has to wait before receiving customer evaluation data (e.g., eye health report, diagnoses, optical prescriptions, etc.) from a remote practitioner.

According to certain embodiments, some or all of the practitioner data may be obtained, tracked and/or updated on a regular, periodic or real-time basis using various mechanisms. For example, in certain embodiments, RPM server 24 (and/or the CDC servers or customer diagnostic centers) may regularly query the remote practitioners (e.g., by sending an e-mail to the remote practitioners each week) in order to request that the remote practitioners provide and/or update certain information, such as their upcoming schedules or periods of unavailability. In certain other embodiments, such as where the remote practitioners can review and/or respond to customer examination data through a web-based service or client application, the remote practitioners may be prompted to provide and update this information when they access the service or application (e.g., when they login to a website or launch an application on their device, etc.). Similarly, in the case where real-time connections are established between the remote practitioner devices and customer diagnostic centers, RPM server 24 (and/or the CDC servers or customer diagnostic centers) may update certain of this information in real-time, such as by keeping track of whether each remote practitioners is logged in to the system and/or currently connected to a customer diagnostic center. Additionally, or alternatively, some or all of the practitioner data may be obtained, tracked and/or updated based on information received or accessed from third party sources, such as accessing a remote practitioner's work schedule (e.g., from a doctor's office or hospital associated with the remote practitioner) or accessing a scheduling or calendar application on the remote practitioner's device. In certain other embodiments, RPM server 24 may use any other suitable means to obtain and update the practitioner data.

In certain embodiments, the system for providing vision and/or eye health examinations may be provided, at least in part, by a centralized cloud-based system. The cloud-based system may be accessible via a web browser (or other application) and may be compatible across all web platforms and devices. Both remote practitioners and users at customer diagnostic center 10 (and/or from other devices, such as a home computer) may login to the cloud-based system when utilizing the system. The cloud-based system may facilitate the exchange of audio/video streams between remote practitioner devices 30 and customer diagnostic centers 10, and may provide various interfaces for display on remote practitioner devices 30 and devices located at customer diagnostic center 10. For example, interfaces may be provided via remote practitioner device 30 for manipulating and controlling the equipment (e.g., the equipment illustrated in FIGS. 4 and 5) located at customer diagnostic center 10, for transmitting customer evaluation data and/or eye health reports to customer diagnostic centers 10, for saving data to a server, for accessing customers' medical records, for communicating with customer diagnostic centers 10 (e.g., via instant messaging, voice, video or other means), and/or for any other features and functionalities related to administering an eye health or vision examination. Likewise, interfaces may also be provided to devices located at customer diagnostic centers 10 for transmitting examination data to remote practitioner devices 30, for saving data to a server, for accessing medical records, for communicating with remote practitioner devices, and/or for any other features and functionalities related to administering an eye health or vision examination.

Although a particular number of remote practitioner devices, CDC servers and customer diagnostic centers are shown in FIG. 2 for illustrative purposes, it should be understood that the eye testing and evaluation system may include any number of these servers and devices. Similarly, while RPM server 24 and practitioner database server 26 are shown in FIG. 2, in certain embodiments, the functionality associated with RPM server 24 and/or practitioner database server 26 may be any number of servers. In certain other embodiments, some or all of the functionality associated with RPM server 24 and/or practitioner database server 26 may be integrated with one or more of CDC servers 20A-20C and/or customer diagnostic centers 10A-10E.

Customer Diagnostic Center

Figure 3:
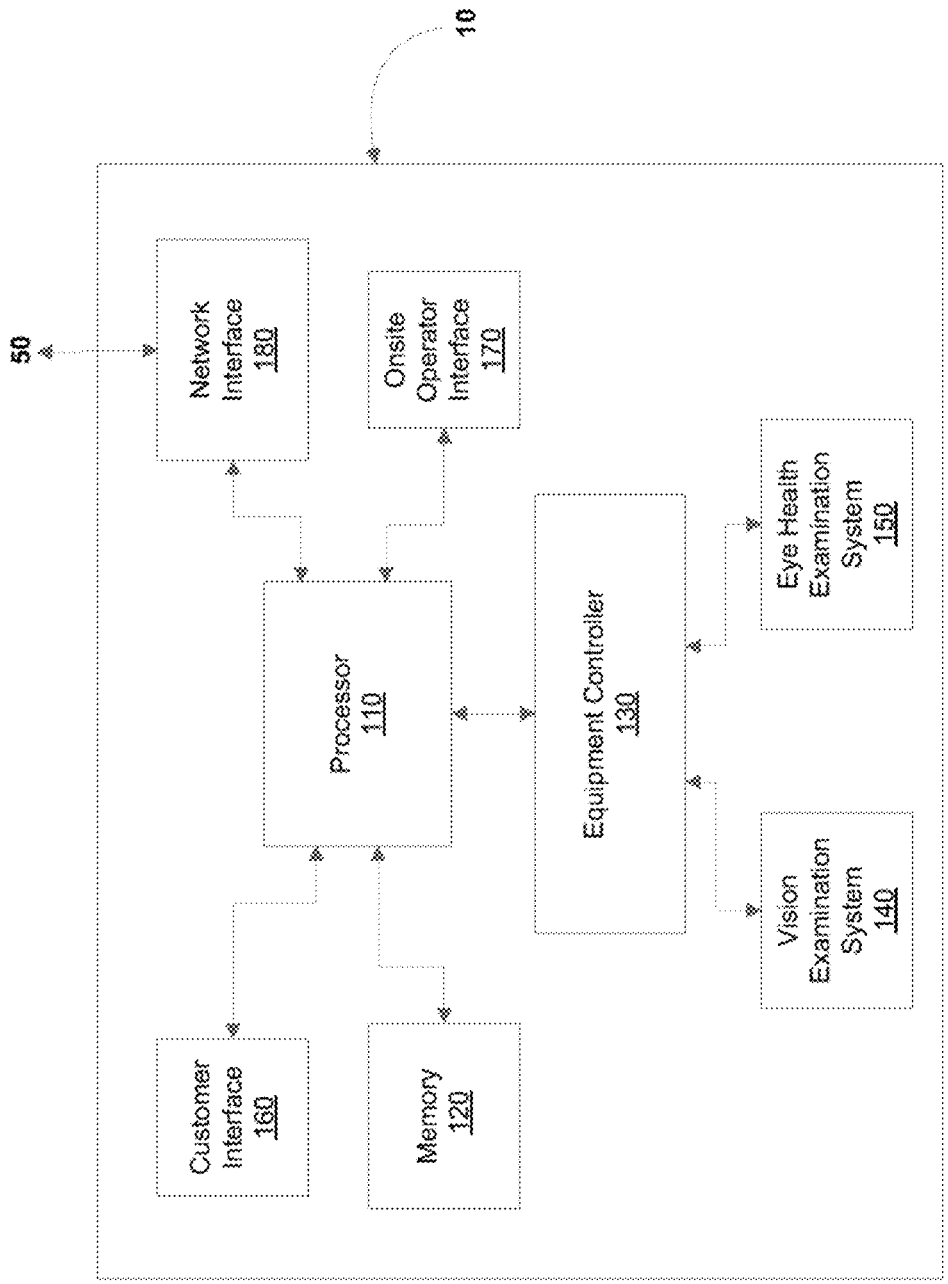
FIG. 3 is a block diagram illustrating a portion of the components of a customer diagnostic center that may be used with the eye testing and evaluation system in accordance with certain embodiments.
Figure 4:
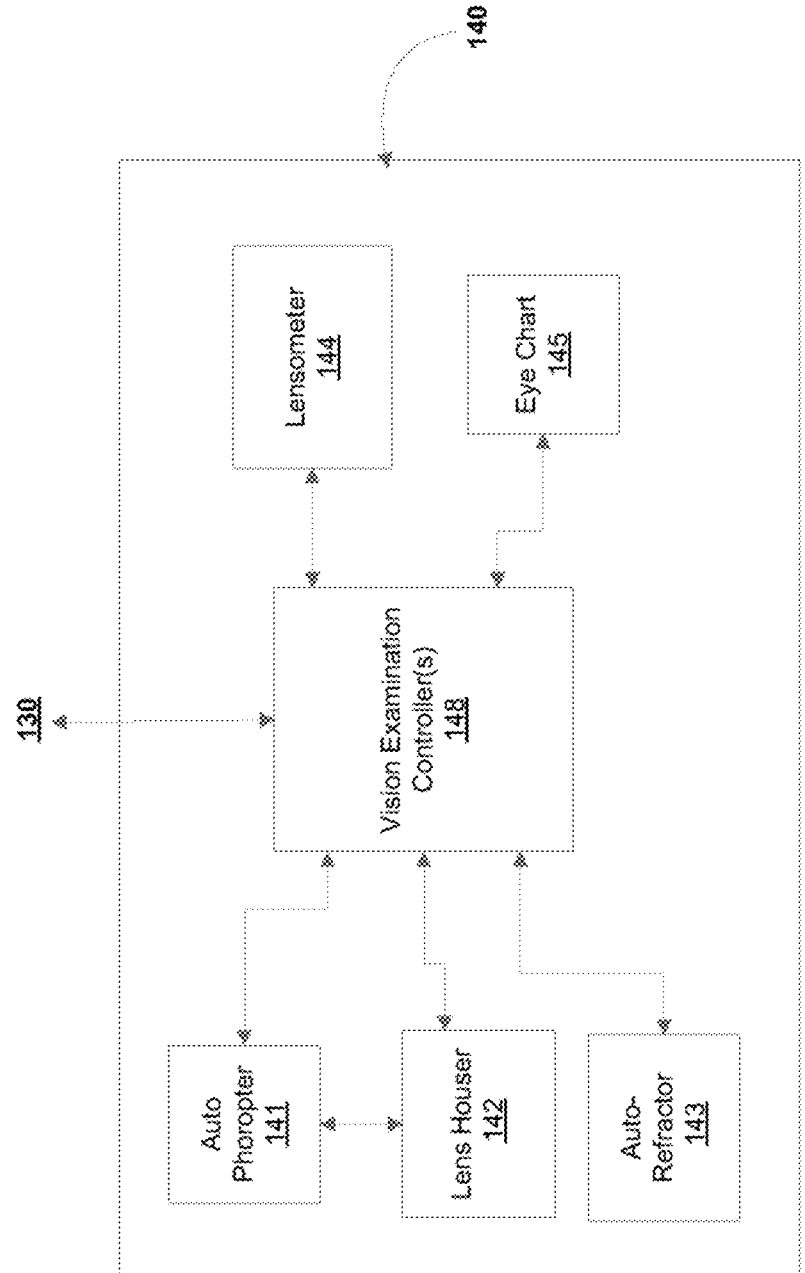
FIG. 4 is a block diagram illustrating a portion of a customer diagnostic center having a vision examination system in accordance with certain embodiments of the present invention.
Figure 5:
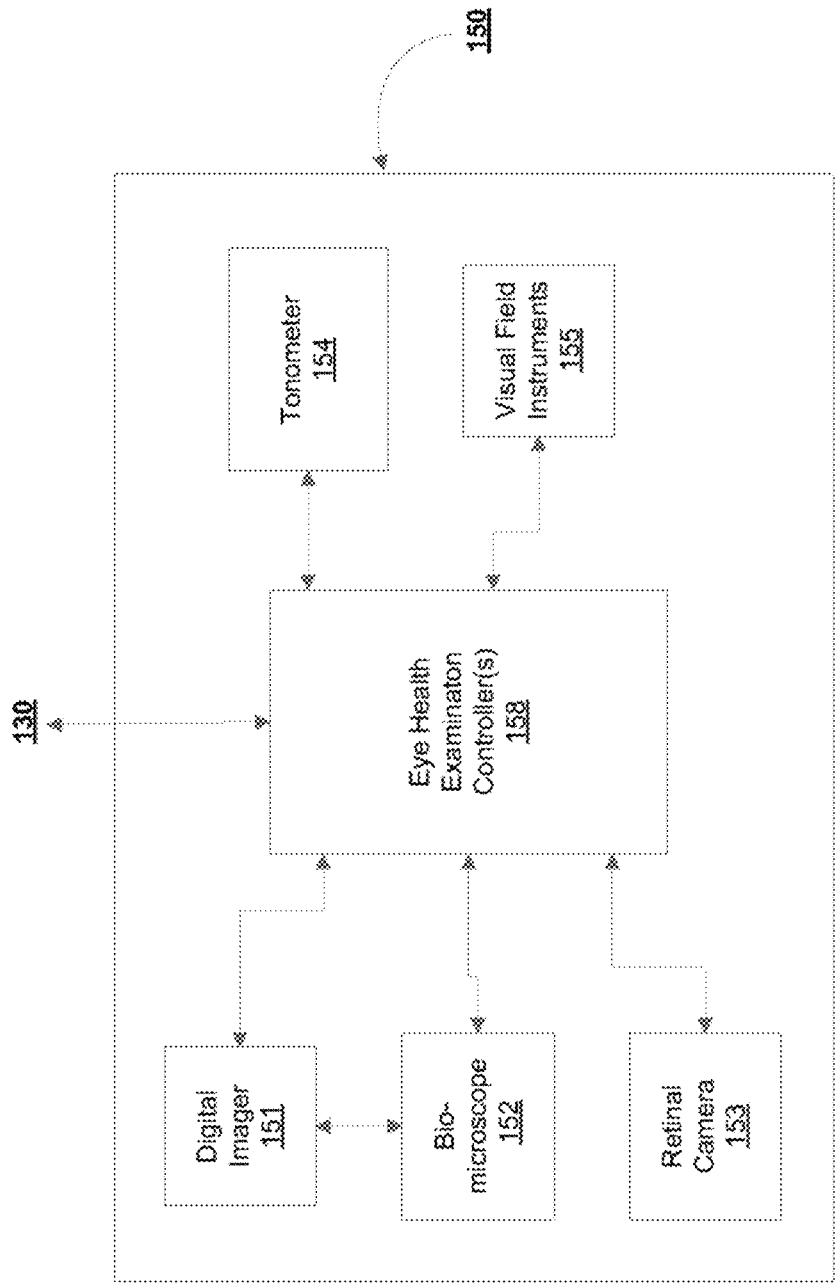
FIG. 5 is a block diagram illustrating a portion of a customer diagnostic center having an eye health examination system in accordance with certain embodiments of the present invention.

FIG. 3 is a block diagram illustrating a portion of the components of a customer diagnostic center that may be used with the eye testing and evaluation system in accordance with certain embodiments. As mentioned above, the customer diagnostic centers provided with the eye testing and evaluation system may be implemented through various types of structures and physical arrangements. Likewise, the customer diagnostic centers may include a wide range of components, such as general hardware components, mechanical devices, electronic equipment, computer hardware and software and any other suitable components for allowing customers to receive eye health examinations and/or vision examinations through the customer diagnostic centers. It should be understood that the particular components described below and/or illustrated in FIGS. 3-5 are intended to be exemplary in nature, not exhaustive, and various other components may be included with the customer diagnostic centers that are provided in connection with the eye testing and evaluation system, corresponding arrangements and systems and methods described herein.

As shown in FIG. 3, in certain embodiments, customer diagnostic center 10, generally includes processor 110, memory 120, equipment controller 130, vision examination system 140, eye health examination system 150, customer interface 160, onsite operator interface 170 and network interface 180. Processor 110 may be responsible for managing the overall operation of customer diagnostic center 110 and/or controlling some or all of the components included therein. In certain embodiments, processor 110 may be a single processing unit, such as a CPU or microcontroller, or may be a computing device, such as a personal computer or workstation. In certain other embodiments, processor 110 may be in the form of multiple processing units, computing devices or any combination thereof. Memory 120 may be used to store and retrieve a wide range of data, such as software, programs and/or instructions executed by processor 110 (or other components) and/or data generated, received and used by various components of customer diagnostic center 10. Memory 120 may include any known type of data storage device and/or media, such as magnetic media, optical media, random access memory, read-only memory, data cache, etc., or any combination of one or more data storage devices and media. In certain embodiments, memory 120 (or a portion thereof) may be integrated with one or more other components of customer diagnostic center 10, such as processor 110.

Vision examination system 140 may include various ophthalmic devices, equipment, and instruments (e.g., refractors, phoropters, lensometers, etc.), and/or other associated systems, devices, components, and/or computer hardware, software and data that allow customers to receive vision examinations at customer diagnostic center 10. In certain of these embodiments, vision examination system 140 may be used in connection with administering a number of tests and procedures to customers and measuring, capturing and/or generating various data associated with determining the customers' visual acuity and/or evaluating certain other aspects of the customers' vision. Similarly, eye health examination system 150 may include various ophthalmic equipment (e.g., tonometers, digital imagers, biomicroscopes, etc.) and/or other associated components that allow customers to receive eye health examinations at customer diagnostic center 10. In certain of these embodiments, eye health examination system 150 may be used in connection with administering a number of tests and procedures to customers and measuring, capturing and/or generating various data associated with evaluating the customers' eye health.

Although vision examination system 140 and eye health examination system 150 are shown in FIG. 3, it should be understood that, in certain embodiments, this may be a logical rather than a physical distinction. In other words, in certain of these embodiments, some or all of the ophthalmic equipment and associated components may be used in connection with both vision examinations and eye health examinations. Examples of the types of ophthalmic devices, equipment and instruments and associated components that may be included in vision examination system 140 and eye health examination system 150, along with various tests and procedures that may be administered to customers using such equipment, are further illustrated and described below in connection with FIGS. 4 and 5.

Equipment controller 130 may be responsible for controlling the operation of vision examination system 140 and/or eye health examination system 150. In certain embodiments, this may include controlling some or all of the ophthalmic equipment and associated components in a number of ways, such as turning equipment on and off, initializing and setting up the equipment, moving and positioning the equipment, and/or instructing the equipment to perform various operations and procedures. In certain embodiments, equipment controller 130 may include a single processing unit, microcontroller, or computing device that controls some or all of the ophthalmic equipment and associated components of vision examination system 140 and/or eye health examination system 150. In certain other embodiments, equipment controller 130 may include a number of processing units, microcontrollers and/or computing devices, each of which is responsible for controlling one or more of the ophthalmic devices, instruments, equipment, and/or associated components. In yet other embodiments, some or all of the functionality associated with equipment controller 130 may be integrated with various other components, such as processor 110 or onsite operator interface 170. For example, in certain of these embodiments, equipment controller 130 and/or processor 110 may be in the form of (or include) a personal computer, workstation, or similar computing device, which is connected (physically and/or wirelessly) to some or all of the ophthalmic equipment and associated components included in vision examination system 140 and/or eye health examination system 150.

According to certain embodiments, equipment controller 130 may include and execute various software, programs and/or instructions associated with controlling the operation of the ophthalmic equipment and associated components. For example, equipment controller 130 may run one or more programs that include instructions for setting up the equipment and/or using the equipment to administer a number of tests and procedures in response to a customer requesting a vision examination and/or eye health examination through customer diagnostic center 10. In certain of these embodiments, equipment controller 130 may retrieve the software, programs and/or instructions from memory (such as memory 120) execute the programs on an as-needed basis or when instructed to do so by processor 110. In certain embodiments, such as where the ophthalmic equipment and/or test administration can be monitored and controlled by various individuals (e.g., a remote practitioner, off-site technician, and/or on-site operator) equipment controller 130 may also (or instead) receive instructions, or execute instructions based on input received, from various other components of customer diagnostic center 10. In certain of these embodiments, for example, equipment controller 130 may receive instructions or input from a remote practitioner and/or offsite technician (e.g., remote practitioner's assistant, remote equipment operator) via network interface 180, of from an on-site operator or technician via on-site operator interface 170.

As shown in FIG. 3, in certain embodiments customer diagnostic center 10 may include on-site operator interface 170, which may allow an operator, technician, examination assistant, or any other suitable individual, who is at the same location as the customer diagnostic center to control certain aspects of the customer diagnostic center. In certain embodiments, for example, on-site operator interface 170 may allow the on-site technician to control and/or monitor some or all of the ophthalmic equipment and associated components included with vision examination system 140 and eye health examination system 150 and/or the tests and procedures administered to customers using the equipment. In certain of these embodiments, the on-site technician may control, modify, and customize the equipment, tests and/or information output to customers during the tests for a particular customer, such as based on one or more responses or selections provided by the customer or in response to various data, measurements and results obtained through the tests. As another example, on-site operator interface 170 may enable the on-site technician to control and monitor other operations of customer diagnostic center 10, such as to assist customers with creating an account, accessing and updating prior test reports and customer data, forwarding information to third parties (e.g., sending test reports or optical prescriptions to an external practitioner or lens lab), and/or ordering and purchasing eye care and vision related products and services from an online retailer.

In certain embodiments, on-site operator interface 170 may include various input/output devices and components that enable an on-site technician to monitor and control the operations of customer diagnostic center 10. In certain of these embodiments, for example, on-site operator interface 170 may include one or more displays, touch screens, speakers, voice recognition systems, keyboards, touch pads, mice, joysticks, microphones, and/or any other suitable input/output devices and components for displaying or otherwise outputting information to the on-site technician (e.g., equipment status, examination data and results, customer inputs and responses, etc.) and/or receiving selections and inputs from the on-site technician (e.g., commands, instructions, data to be output to the customer, etc.). In certain embodiments, such as where equipment controller 130 and/or processor 110 are in the form of (or include) a personal computer or workstation, on-site operator interface 170 may comprise various standard input/output components and peripheral devices that are integrated with (or connected to) the personal computer (e.g., monitor, keyboard, mouse, etc.). On-site operator interface 170 may also include computer software, applications and/or programs that assist the on-site technician with the process of monitoring and controlling the operations of the customer diagnostic center. For example, on-site operator interface 170 may provide one or more applications that allow on-site technicians to make various selections, input data and commands, and/or view information pertaining to certain components of the customer diagnostic center through a graphical user interface.

Customer interface 160 may be used to display information and data to, and receive various inputs, selections, and responses from the customers. Like on-site operator interface 170, customer interface 160 may include any suitable input/output devices and components, (e.g. touch-sensitive and/or other types of display screens, microphones, speakers, keyboards, mice, etc.) that enable customers to, and assist customer with, requesting and receiving vision examinations and/or eye health examination and accessing various other features and functionality provided through customer diagnostic center 10.

For example, in connection with a customer accessing customer diagnostic center 10, customer interface 160 may display one or more questions, forms, options, prompts or the like that allow the user to access, view, input, modify, and/or update various information associated with the customer (e.g., user login information, account data, customer data, prior examination reports, results and data, etc.). Similarly, in certain embodiments, customer interface 160 may present customers with various options concerning the services that can be obtained through customer diagnostic center. In certain of these embodiments, customers may be able to select an option to receive a vision examination, eye health examination or both. In certain other embodiments, customers may be able to choose from one or more predefined vision examination and/or eye health examination services (e.g., services associated with different levels, costs, time requirements) and/or create a customized vision examination and/or eye health examination by selecting one or more specific tests and procedures to be included in the desired service. In certain embodiments, the customer interface 160 may display options for transmitting a request for selecting a practitioner to administer an vision or eye health examination. In certain embodiments, the customer interface 160 may display options for selecting a practitioner for administering an vision or eye health examination and the request transmitted from the customer diagnostic center may identify one or more practitioners. In certain embodiments, a request for an vision or eye health examination may be received at a server and the server may select one or more practitioners to receive the request.

As another example, in connection with administering various eye health and vision tests to a customer, customer interface 160 may display various information to the customer, such as data used to perform the tests (e.g. eye-charts, testing images and graphics), data associated with requesting the customer to provide certain responses, selections and inputs (e.g., test questions, forms, etc.), and/or data pertaining to testing instructions or directions (e.g., instructing the customer to stand, sit, or assume a particular position, blink, look in a certain direction, etc.). In turn, customer interface 160 may receive various data from the customer during the tests, such as responses to test questions.

As yet another example, after a customer has received an eye health examination and/or vision examination through customer diagnostic center 10 (or another customer diagnostic center), customer interface 160 may display various information pertaining to the tests, such as results, diagnoses, recommendations and other data that is automatically generated by customer diagnostic center 10 (and/or a CDC server associated therewith), or data received from a remote practitioner (e.g., eye-health reports, optical and other prescriptions, diagnoses, recommendations, referrals). In addition, as discussed in more detail below, a wide variety of data and information may also be displayed to and received from customers through customer interface 160 in connection with numerous other features and functionality, such as paying for services received through the customer diagnostic centers, requesting data to be forwarded to one or more third parties, viewing, ordering and purchasing eye-care and vision products and services, and/or communicating with remote practitioners and other third parties.

In certain embodiments, customer interface 160 may include various software, applications and programs for managing the output of information to customers and/or assisting customers with the process of inputting and providing data, responses, etc. In certain of these embodiments, these applications may provide customers with a user-friendly graphical user interface that allows the customers to access and view information, input text and other data, and make selections, such as through a touch screen, keyboard, mouse or the like.

According to certain embodiments, customer interface 160 may include an audio response system, which may comprise and utilize various systems, devices, and software, such as speakers, microphones, voice recognition software, text-to-voice software, etc. In certain of these embodiments, the audio response system may be used to output various information and data to and/or receive various inputs, selections and data from the customers in the form of voice and/or other suitable audio data. In certain of these embodiments, the audio response system may be utilized in addition to (or instead of) outputting and receiving some or all of the data through other mechanisms, such as displays, keyboards, etc. For example, the audio response system may be used in connection with the administration of one or more eye health and/or vision tests, such as to ask the customer questions, receive responses and selections from the customer, and/or provide instructions and directions to the customer. In certain of these embodiments, the questions or other audio outputs may be based on a stored set of predefined questions and/or may be selected or determined based on the customer's responses to previous questions or the measurements or results of prior tests or procedures administered to the customer.

In certain embodiments, customer diagnostic center 10 may include network interface 180, as shown in FIG. 3. Network interface 180 may include any known networking devices, computer hardware and software, and/or associated systems and components, that enable customer diagnostic center 10 to send and receive data via one or more networks. In certain of embodiments, network interface 180 may provide interfaces that allow customer diagnostic center 10 to communicate with (and/or connect to) various other systems and devices (e.g., CDC servers, remote practitioner devices, third party retailer systems, etc.) over a wide range of networks (e.g., network 50). In certain of these embodiments, network interface 180 may also (or alternatively) be responsible for facilitating, controlling and/or managing some or all of the communications. For example, network interface 180 may facilitate and/or manage the communication of various data to and from CDC servers (e.g., customer data, testing data and programs, software and firmware updates, etc.), and remote practitioner devices (e.g., customer data, customer examination data, customer evaluation data, etc.).

According to certain embodiments, network interface 180 may include various systems, software and other components that allow for the encryption and encoding of some or all of the communications sent from the customer diagnostic center to be encrypted or encoded prior to transmission (as well as the decryption and decoding of communications received by the customer diagnostic center). For example, customer diagnostic center 10 may encrypt and/or encode all transmissions that include medical data for the customers (e.g., customer examination data, prior test results, etc.), or may encrypt and/or encode all transmissions having any data that is associated with the customers. In certain of these embodiments, the data and/or communications may be encrypted and/or encoded using any know methods and mechanisms.

Although FIG. 3 illustrates a exemplary portion of the systems, devices, and components that may be included in customer diagnostic center 10, in certain embodiments some or all of the customer diagnostic centers provided through the eye system may include various other systems, devices, and components (not shown in FIG. 3). For example, the customer diagnostic centers may include one or more recording devices, systems, and/or associated software (e.g., cameras, video cameras, audio recorders, etc.) that enable the customer diagnostic centers to capture and record various data associated with the administration of the tests and procedures to customers. In certain embodiments, such as where the customer diagnostic centers communicate with a remote practitioner and/or off-site technician, this data may be sent to these individuals along with (or instead of) customer data and/or customer examination data, such as to allow the remote practitioner to view the customers, view or hear responses from the customers, and/or to determine whether certain equipment was setup and operated appropriately and whether one or more tests were administered properly. In certain of these embodiments, such as where a real-time connection is established between the customer diagnostic centers and the remote practitioner devices, the recording system may allow the customer to interact with the remote practitioner in real-time (e.g., through an audio/video conferencing system or the like).

As another example, the customer diagnostic centers may include various payment related devices, systems, and/or software (e.g., credit/debit card readers, devices for depositing cash or checks, etc.) that allow the customer diagnostic center to receive payments from customers, such as in connection with providing customers with eye health examinations, vision examinations, and/or other services (e.g., ordering products and services from third parties). As yet another example, the customer diagnostic centers may include a number of other devices and systems for providing information to customers, such as printers, and/or for allowing customers to upload and input information, such as scanners, card readers, USB key readers, etc.

Additionally, some or all of the components shown in FIG. 3, may be omitted from customer diagnostic centers provided through the eye testing and evaluation system, or may be replaced with one or more other components. For example, in certain embodiments, some or all of the customer diagnostic centers may be implemented without the use of an on-site operator interface, and/or may include only one of vision examination system 150 or eye health examination system 140.

Vision Examination System

FIG. 4 is a block diagram illustrating a portion of a customer diagnostic center having a vision examination system in accordance with certain embodiments. As discussed above, in certain embodiments, some or all of the customer diagnostic centers provided with the eye testing and evaluation system may include a vision examination system. The vision examination system may comprise various ophthalmic devices, equipment and instruments, and other general hardware, mechanical and electronic devices and/or computer software and hardware that is utilized by the customer diagnostic center to provide vision examinations to customers. For example, as shown in FIG. 4, vision examination system 140 may include auto-phoropter 141, lens houser 142, auto refractor 143, lensometer 144, eye chart 145, and vision examination controller 148.

In certain embodiments, auto-phoropter 141 may comprise any suitable type of phoropter and/or other similar device (or a number of such phoropters and devices) that can be used to present powered lenses in front of a customer's eyes. Lens houser 142 may include one or more devices that are used to house and maintain a number of powered lenses and/or allow the lenses that are presented through auto-phoropter 141 to be switched in and out. In certain embodiments, lens houser 142 includes a wide range of powered lenses having different sphere, cylinder and/or axis values. Although, auto-phoropter 141 and lens houser 142 are shown as separate components in FIG. 4, in certain other embodiments, lens houser 142 (or a portion thereof) may be integrated with auto-phoropter 141.

Auto-refractor 143 may include one or more suitable types of refractors and/or similar devices that can be used to measure the refractive error of a customer's eyes. In certain of these embodiments, auto-refractor 143 may allow the system to determine approximate objective optical error specifications for sphere, cylinder and axis for one or both of the customer's eyes and/or measure curvatures in the steepest and flattest meridians of the corneas. In certain embodiments, vision examination system 140 may include an auto-keratometer, which may be integrated with auto-refractor 143, for measuring "K readings" that may be used to determine back or base curvature of a customer's lenses. Lensometer 144 may comprise one or more suitable types of lensometer and/or similar devices that can be used to measure and determine the power of optical lenses that are included in a pair of eye-glasses or contact lenses (e.g., the customer's current glasses). Eye chart 145 may be in the form of one or more charts, images, or the like, that can be presented to customers during various vision examination tests, such as to aid in determining the customer's visual acuity. In certain of these embodiments, eye chart 145 may include one or more physical eye charts and/or virtual eye charts (e.g., charts or images that are displayed on a computer screen or electronic display).

As shown in FIG. 4, in certain embodiments, vision examination system 140 may also include vision examination controller 148, which may comprise one or more processing units, microcontrollers, computing devices, hardware and software, and/or mechanical and electrical devices and components that control the operations of the vision examination equipment. In certain embodiments, vision examination controller 148 may be connected to and/or communicate with equipment controller 130 to allow the vision examination equipment to be monitored and/or controlled by the customer diagnostic center and/or one or more individuals (e.g., on-site operator). In certain other embodiments, vision examination controller 148 (or a portion thereof) may be integrated with equipment controller 130 and/or the vision examination equipment (e.g., auto-phoropter 141, lensometer 144, etc.).

In certain embodiments, some or all of these (and other) components may be used by the customer diagnostic center in connection with administering a variety of tests and procedures to customers, such as in order to measure, capture and/or record data pertaining to a customers' visual acuity and/or visual ability. For example, some or all of these components may be used in order to perform an automated refraction process that allows the refractive error of a customer's eyes to be determined. The following description is intended to demonstrate the type of steps and operations that may be included in an exemplary automated refraction process performed by a customer diagnostic center in accordance with certain embodiments.

In response to a customer requesting a vision examination, the customer diagnostic center may determine a preliminary refractive error or error range for the customer's eyes. In certain embodiments, the preliminary error may be determined based on various data associated with the customer, such as prescriptions or refractive errors associated with one or more prior vision examinations received by the customer (e.g., through a customer diagnostic center and/or from various practitioners) that is retrieved from customer data (e.g., stored in local memory or at a CDC server or database server). Alternatively, or in addition, the customer diagnostic center may use lensometer 144 to determine the preliminary refractive error by measuring the power of the lenses in a current pair of eyeglasses or contact lenses provided by the customer. In certain of these embodiments, the preliminary refractive error may be used in the automated refraction process in various manners, such as to determine a starting point for other tests or calculations or to confirm or check that the process was performed properly (e.g., to check that the ultimate determination for the refractive error does not conflict with or seem highly improbably in light of the customer's prior refractive error). The customer diagnostic center may also (or instead) measure the refractive error of the customer's eyes using auto-refractor 143.

The customer diagnostic center may then use auto-phoropter 141, lens houser 142 and/or eye chart 145 to administer an interactive refraction test to the customer. In certain embodiments, this may include an iterative process in which powered lenses are placed in front of the customer's eyes using auto-phoropter 141 and/or lens houser 142, questions are presented to and responses are received from the customer using the customer interface (e.g., through the audio response system), and based on the customer's responses, the powered lenses are switched with lenses having a different power, and so on. The questions may include asking the customer to read information displayed on eye chart 145 and/or asking the customer whether the displayed information appears clearer or less clear with the current powered lenses. In certain of these embodiments, the questions may be retrieved from a predefined set of stored questions and/or based on the customer's responses to previous questions. This iterative process may continue until one or more conditions or criteria are met, such as receiving a particular combination of responses from the customer, or determining that sufficient data has been acquired through the test.

In certain embodiments, after performing these tests and measurements (or at one or more points during the process) the customer diagnostic center may record and/or store various types of data, such as the questions presented to and responses or inputs received from the customer, the tests, operations and steps performed, the results of the measurements, calculations performed, etc. In turn, some or all of this data may be stored locally and/or sent to a CDC server to update the customer data and other information associated with the customer. The customer diagnostic center may then determine an updated refractive error for the customer's eyes, such as by making various calculations and applying one or more predefined algorithms to the examination data and/or other data (e.g., customer data). In certain embodiments the customer diagnostic center may package and/or format some or all of the examination data and customer data, together with the final refractive error and other information (e.g., potential disorders, defects or conditions detected by the customer diagnostic center based on the examination data), and send the packaged data to a remote practitioner for review and confirmation. In response, the customer diagnostic center may receive customer evaluation data (e.g., revised refractive error, optical prescription, recommendations, referrals to see other practitioners, etc.) from the remote practitioner.

In certain other embodiments, the customer diagnostic center may establish a connection with the remote practitioner prior to, during, or after performing the automated refraction procedure, such as to allow the remote practitioner to monitor and control the tests, view and interact with the customer, review and analyze the examination data, and/or provide the evaluation data in real-time. In yet other embodiments, the customer diagnostic center may automatically generate customer evaluation data based on the updated refractive error, examination data and/or customer data. After generating or receiving the customer evaluation data, the customer diagnostic center may provide the customer evaluation data (or a portion of it) to the customer, such as by displaying information to the customer and/or providing the customer with one or more printed documents (e.g., an optical prescription) at the customer diagnostic center, or sending information to the customer (e.g., via e-mail).

As can be seen from the foregoing, the automated refraction procedure performed through the customer diagnostic center may include both an objective portion (e.g., using auto-refractor 143 to measure the customer's objective refractive error and/or lensometer 144 to measure the power of the customer's current lenses), and a subjective portion (e.g., using auto-phoropter 141, lens houser 142, eye chart 145 and/or an automated voice response system to present powered lenses in front of the customer's eyes and ask the customer questions and receive subjective responses from the customer pertaining to the customer's perceived visual acuity with such powered lenses). In a similar manner, various other vision examination and/or eye health tests and procedures performed by the customer diagnostic center may include both objective and subjective components. One important benefit to using these types of tests is that the accuracy of the tests and the corresponding results is often significantly higher as compared to similar tests that only utilize an objective or subjective process.

The exemplary automated refraction process discussed above is intended to be illustrative, not limiting, and it should be understood that, in certain other embodiments, one or more of the described steps or operations could be removed, reordered, or modified, or could be replaced with one or more other steps or operations, and various other steps and operations may be added to the process. Also, the vision examination system illustrated in FIG. 4 may be used by the customer diagnostic center to perform various other tests and procedures associated with the examination of a customer's vision. Likewise, the vision examination system may be modified, such as by omitting, updating or replacing one or more of the components shown in FIG. 4 and/or including other ophthalmic equipment, devices, instruments, and/or other associated components, in order to incorporate new or update existing vision examination equipment, tests and procedures.

For example, vision examination system 140 may include an electronic visual acuity monitor for allowing the system to perform various tests associated with measuring a customer's visual acuity at longer distances. In certain embodiments, the electronic visual acuity monitor may be used to determine the size of objects at specific distances that are visually perceptible to a customer (e.g., 20/20 or 20/30 size letters or other object). In certain of these embodiments, the electronic visual acuity monitor (or a portion of it) may be integrated with eye chart 145, such as in the form of a Snellen 'E' chart in a self-lit visual acuity monitor. In certain embodiments, the electronic visual acuity monitor may be used to administer various tests to measure digital visual acuity data for a customer with and/or without lenses at various distances, based on subjective responses and inputs received from the customer, which can be compared to certain measurement standards. In certain of these embodiments, the measurements and results of such tests may allow the system to assess changes in the customer's vision, such as in response to a new set of lenses or treatments received by the customer (e.g., medicine or surgery).

Eye Health Examination System

FIG. 5 is a block diagram illustrating a portion of a customer diagnostic center having an eye health examination system in accordance with certain embodiments. As discussed above, in certain embodiments, some or all of the customer diagnostic centers provided with the eye testing and evaluation system may include an eye health examination system. The eye health examination system may comprise various ophthalmic devices, equipment and instruments, and other general hardware, mechanical and electronic devices and/or computer software and hardware that is utilized by the customer diagnostic center to provide eye health examinations to customers. For example, as shown in FIG. 5, eye health examination system 150 may include digital imager 151, biomicroscope 152, retinal camera 153, tonometer 154, visual field instruments 155, and eye health examination controller 158.

In certain embodiments, digital imager 151 may comprise any suitable type of digital imaging device, such as a camera, video-camera, sonar imager, infrared imager, or other similar digital imager (or a number of such devices) that can be used to capture, record and/or generate digital images of a customer. For example, digital imager 151 may be used to obtain full facial images of a customer, and/or various proportionate, to-scale, images of the customer's eyes, pupils, face, or head (e.g., a full facial image). Biomicroscope 152 may be in the form of any suitable type of microscope or microscopes that are used to magnify the view of the anterior portion of a person's eyes (e.g., the first third of a person's total eye length). In certain embodiments, biomicroscope 152 and/or digital imager 151 may be used to detect, and capture images related to, various tissue enhancements (e.g. from the tear layer, cornea, aqueous/anterior chamber, lens, and/or posterior chamber).

In certain embodiments, retinal camera 153 may comprise any suitable type of camera or other like device that allows for enhanced viewing and/or digital imaging of the rear portion of a person's eyes (e.g., the back two third's of a person's total eye length). For example, retinal camera 153 may be used to detect, and capture images related to, the vitreous, choroids, retina, macula, and/or optic nerve of a person's eyes. A tonometer 154 may also be used. Tonometer 154 may include any suitable device or device that can be used to measure the intraocular pressure of a person's eyes, such as to detect, diagnose, and/or evaluate the possibility of glaucoma. In certain of these embodiments, for example, tonometer 154 may allow intraocular pressure to be determined in millimeters of mercury (mmHG), such as by detecting the degree of indentation (e.g., resistance) of a probe at a ninety degree angle flat to the center of a person's cornea and using this measurement to calculate mmHG based on one or more predefined formulas.

Eye health examination system 150 may also include various visual field instruments, such as visual field instruments 155 illustrated in FIG. 5. In certain embodiments, visual field instruments 155 may comprise one or more instruments and devices that can be used to detect and measure visual sensitivity and/or acuity in a person's peripheral view (e.g., things surrounding an object upon which a person's vision is primarily fixed or focused). For example, in certain of these embodiments, visual field instruments 155 may be used to flash various visual stimuli of different light-candle strengths in a customer's periphery while the customer's vision is focused on an object that is straight-ahead. In turn, such tests can determine the existence of various defective fields of vision, such as patterns of non-discernable vision within a world-view having four, equal and symmetric quadrants (e.g., a person's blind spot, where there are no rods and cones), which can be used to detect, diagnose, and/or evaluate certain conditions and disorders (e.g., advancing glaucoma, detached retina, tumors, diabetic retinopathy, or retinitis pigmentosa).

As shown in FIG. 5, in certain embodiments, eye health examination system 150 may also include eye health examination controller 158, which may comprise one or more processing units, microcontrollers, computing devices, hardware and software, and/or mechanical and electrical devices and components that control the operations of the eye health examination equipment. In certain embodiments, eye health examination controller 158 may be connected to and/or communicate with equipment controller 130 to allow the eye health examination equipment to be monitored and/or controlled by the customer diagnostic center and/or one or more individuals (e.g., on-site operator). In certain other embodiments, eye health examination controller 158 (or a portion thereof) may be integrated with equipment controller 130 and/or the eye health examination equipment (e.g., digital imager 151, tonometer 154, etc.).

In certain embodiments, some or all of these (and other) components may be used by the customer diagnostic center in connection with administering a variety of tests and procedures to customers associated with evaluating the customers' eye health. For example, the customer diagnostic center may use some or all of the eye health examination equipment to measure, capture and record customer examination data pertaining to a customer's eye health, process, analyze and evaluate the customer examination data, package and deliver the customer examination data to a remote practitioner for review, receive customer evaluation data from the remote practitioner and/or provide an eye health report to the customer, in a similar manner to the automate refraction process described above.

The following provides certain examples of ophthalmic equipment, devices, instruments, and components, as well as tests and procedures that may be incorporated with the eye health examination system and offered to customers through the customer diagnostic centers in accordance with certain embodiments. It should be understood that the particular equipment and tests described below are intended to be exemplary in nature, not exhaustive, and various other equipment and tests may be used in connection with the eye health examination system, corresponding arrangements and systems, devices and methods described herein. For example, like the vision examination equipment discussed above, the eye health examination system may be modified, such as by omitting, updating or replacing one or more of the components shown in FIG. 5 and/or including numerous other types of ophthalmic equipment, devices, instruments, and/or other associated components. As another example, the eye health examination system may be periodically updated and/or expanded in order to incorporate new or modify existing eye heath examination equipment, tests and procedures, thereby providing customers with a wide range of the most up-to-date equipment, tests and procedures associated with examining eye health.

In certain embodiments, the eye health examination system may include one or more of the following ophthalmic devices, instruments and equipment and/or may utilize one or more of the following tests and procedures in connection with providing customers with eye health examinations through the customer diagnostic centers:

Pachymeters/Tomographers—one or more pachymeters, tomographers, and similar devices and instruments may be included, such as an ultrasound pachymeter, optical coherence tomographer (OCT), optical coherence pachymeter (OCP), computerized corneal topographer, corneal waveform device (CWF), anterior segment optical coherence tomographer and/or ultrasound biomicroscope. In certain embodiments, these and other devices may be used for taking measurements and performing various tests associated with the cornea, optic nerve, and/or retina and examining the anatomic relationship between the lens, iris and cornea (e.g., anterior chamber depth and structures posterior to the iris, position of ciliary body, or cyclodialysis cleft). Ultrasound pachymetry may be used to non-invasively measure corneal thickness by confocal microscopy, ultrasound, optical biometry with a camera, or an OCT and online OCP. Alternatively (or additionally), an ultrasonic transducer may be utilized to touch the cornea and/or a CWF may be used to capture an ultra-high definition echogram. OCT may be used for low coherence interferometry to evaluate optic nerve and retinal nerve fiber layer (RNFL) thickness (e.g., measured in the peripapillary region with circular scans centered around the optic nerve head (ONH)). In certain of these embodiments, RNFL thickness measurements may be shown in a TSNIT orientation and compared to age matched controlled individuals. In certain embodiments, these devices and tests may allow the system to monitor changes in a customer's corneas, intraocular pressure, ONH and retina, evaluate changes in eye tissues, and/or determine endothelial cell counts and detect corneal irregularities. In certain of these embodiments, the these devices and tests may be used to confirm diagnoses and monitor outcomes after various types of interventions (e.g., to detect subtle wrinkling of chorioretinal folds in posterior pole that are difficult to assess with direct or indirect ophthalmoscopy).

Potential Acuity Meter (PAM)—a PAM or similar device may be included for use in determining visual potential. For example, in certain embodiments, a PAM having an integrated slit lamp may be used to align and focus microscopic white dots to be viewed by a customer. As another example, the device may be used to focus an acuity chart on a customer's retina to remove lenticular affects and determine macular vision potential.

Scheimpflug Photography/Tomography—a Scheimpflug camera or similar device may be included for performing Scheimpflug photography and/or tomography procedures and the like for evaluating a customer's cornea and other portions of the front of the eye. In certain embodiments, these devices may provide digital images of the anterior chamber angle. In certain of these embodiments, rotating versions of the devices may be included that provide three-dimensional digital imagery. Various software and programs may be utilized to measure specific parameters of the angles. In certain embodiments, these devices and tests may allow the system to detect, diagnose and/or analyze certain types of glaucoma (e.g., narrow/closed angle glaucoma).

Scanning Laser Polarimetry (SLP)—SLP may be used to monitor the RNFL and measure peripapillary RNFL thickness, such as by performing laser scans of the posterior retina and measuring birefringent properties of neurotubules contained within ganglion cell axons. In certain of these embodiments, the RNFL thickness in a circular area around the optic nerve may be determined and/or compared to the "double hump" generally observed in normal individuals, in which the superior and inferior poles have the greatest RNFL thickness as opposed to the nasal and temporal poles. In certain embodiments, a GDx nerve fiber analyzer with variable corneal compensation may be utilized to account for individualized corneal differences.

Heidelberg Retina Tomography (HRT)—HRT may be used to measure optic disc tomography using lasers to scan multiple cross sections images to create and analyze a three-dimensional representation of the optic nerve. In certain embodiments, the 3-D representation may be used to assess thickness, surfaces of the optic cup, calculation of cup-to-disc ratio, rim area, and other optic disc parameters. In certain of these embodiments, HRT may be used to evaluate and monitor glaucoma.

Fundus/Retinal Cameras—one or more fundus cameras and/or retinal cameras may be included, such as mydriatic/non-mydriatic retinal cameras, hybrid digital mydriatic/non-mydriatic retinal cameras, non-mydriatic fundus cameras, autoflourescense cameras. In certain embodiments, these and other devices may be used for fundus photography with and/or without the pupils dilated to create photographs of the interior surface of the eye, including the retina, optic disc, macula, and posterior pole. In certain of these embodiments, these images may be used to evaluate the posterior of the eye and diseases or abnormalities of the retina, choroid, vitreous, optic disc, macula and posterior pole.

Fluorescein Angiography (IVFA)—IVFA and/or phase contrast microscopy may be used to diagnose, evaluate, monitor and/or treat retinal abnormalities (e.g., hypertensive and diabetic retinopathies).

Indocyanine Green Angiography (ICG)—ICG may be used to detect certain abnormalities or diseases not detected through IVFA.

Cachet-Bonnet Anesthesiometer—an anesthesiometer, such as a Cachet-Bonnet anesthesiometer may be included, such as to measure corneal sensitivity and, in turn corneal diseases and abnormalities.

Orbscan/Optical Biometer—an Orbscan or optical biometer may be included for A-scan ultrasound biometry. In certain embodiments, measurements are taken along a visual axis over the curvature of the cornea which may provide data on the length of the eye and/or intraocular lens power. In certain of these embodiments, the measurements may be used to detect common sight disorders.

Tonometer—one or more tonometers or the like may be included, such as an Applation Goldman Tonometer, Non-Applanation Tonometer, Air-Puff Tonometer, Ocular Response Analyzer, Non-Contact Tonometer, Indentation Shiotz, Tono-Pen, Rebound Tonometer, and/or Pascal Dynamic Contor. In certain embodiments, these and other devices may be used for measuring intraocular fluid eye pressure or corneal visco-elasticity, such as to monitor the integrity of the cornea and/or detect certain pathologies, such as keratoconus and glaucoma.

Additionally, in certain embodiments, the eye health examination system may include numerous other types of ophthalmic devices, instruments and equipment and/or may utilize numerous other types tests and procedures in connection with providing customers with eye health examinations through the customer diagnostic centers, including brightness acuity tester, macular photostress test, function vision analyzer, stereopsis testing, color testing (e.g., Ishihara or Farnsworth lantern), pin hole potential acuity testing, contrast sensitivity testing, wavefront aberrometer, refractive power/corneal analyzer, slit lamp biomicroscopy, hand-held slit lamp, the Seidel test with slit lamp, the Van Herick test with slit lamp, Goldman tonometer with slit lamp, oblique flashlight test, swinging flashlight test, exophthalmometer, ERG and mERG, visually evoked response test, electro-oculogram, cover test, ocular motility, Amsler grid, perimeters (e.g., automated static threshold perimeter), Swedish interactive threshold algorithm test, Esterman test on Humphrey perimeter, short-wavelength automated perimetry, frequency doubling technology, Foresee preferential hyperacuity perimeter, pupilometer for pupilar distance, pupilometer for visual stimuli, ophthalmoscope, direct/indirect ophthalmoscope, confocal laser ophthalmoscope, wide-angle twin magnification ophthalmoscope, retinoscope, Schirmer test, dry eye/tear film dysfunction test, radiuscope, optical microspherometer, progressive add lens finder, operating microscope, gonioscope with slit lamp, direct/indirect goniolens, magnetic resonance imaging, nuclear magnetic resonance imaging, magnetic resonance tomography, computed tomography, computed axial tomography.

Varying Levels of Automation and Assistance

As mentioned above, the eye testing and evaluation system may be implemented using different levels of automation and/or different types of assistance from on-site and/or remote individuals. The following describes a number of exemplary implementations having varying degrees of assistance and automation, in accordance with certain embodiments In certain embodiments, for example, the system (or a portion thereof) may be configured to be fully automated, thereby allowing customers to obtain vision examinations and/or eye health examinations at a customer diagnostic center with no assistance from others. In certain of these embodiments, the customer diagnostic centers may utilize and execute software applications, programs and routines that are designed to obtain various information from the customers through the customer interface (e.g., customer data) and determine one or more vision examination and/or eye health examination tests and procedures to administer to the customers (e.g., based on the customers' data and/or selections received from the customer regarding desired services). Likewise, the customer diagnostic centers may utilize and execute software in connection with administering one or more tests to the customer, such as programs that enable the customer diagnostic centers to control and operate the ophthalmic equipment, devices and related components, output instructions, questions, testing data and other information to customers, and/or receive and record responses and inputs from the customers, measurements, readings, and other data resulting from administering the tests and procedures. In turn, after administering the tests and procedures (or during such administration), the customer diagnostic centers may process and analyze the data captured and recorded through the tests, and/or other data (e.g., customer data), using various algorithms, metrics and software in order to automatically evaluate the customers' vision and/or eye health. In certain of these embodiments, the customer diagnostic centers may also utilize and execute various software for auto-generating one or more reports, documents, and the like pertaining to the customers' vision and/or eye health (e.g., eye-health reports, prescriptions, recommendations, referrals, etc.) that can be output and/or provided to the customers.

In certain embodiments, the system (or a portion thereof) may be configured to enable on-site operators (e.g., operators, technicians, or assistants at the sites where the customer diagnostic centers are located) to facilitate and assist customers with one or more aspects of the vision examinations, eye-health examinations, and/or other services, features and functionality provided through the customer diagnostic centers. In certain of these embodiments, for example, the on-site operators may simply assist customers with one or more processes associated with the use of the customer diagnostic centers, such as creating an account, choosing desired services, printing out an eye health or vision report, forwarding data to third parties, etc. As another example, the on-site operators may assist and guide customers during the administration of various tests and procedures, such as by helping customers assume the required positions and answer or respond to certain questions or other data output during the tests. In certain of these embodiments, the on-site operators may provide assistance to customers on an as-needed or as-desired basis, such as in response to a customer selecting an option or otherwise indicating a desire for on-site help.

In certain of these embodiments, the on-site operators may monitor and/or control the ophthalmic equipment and devices (e.g., through an on-site operator interface), such as during one or more tests and procedures to ensure proper administration, and/or before and after the tests and procedures to initialize, setup and/or reset the equipment. Likewise, in certain of these embodiments, the on-site operators may also (or instead) monitor and control the administration of one or more tests, such as by selecting and/or modifying the questions or outputs presented to the customers based on previous responses from the customers and/or test results. In certain other embodiments, some or all of the assistance provided by, and functionality associated with, the on-site operators may be provided by one or more remote operators (e.g., a technician located at a remote call center or an assistant associated with a remote practitioner).

According to certain embodiments, the system (or a portion thereof) may be configured to enable remote practitioners (e.g., practitioners who are not at the sites where the customer diagnostic centers are located) to facilitate and assist customers with one or more aspects of the vision examinations, eye-health examinations, and/or other services, features and functionality provided through the customer diagnostic centers. For example, in certain preferred embodiments, when a customer receives a vision examination and/or eye health examination through a customer diagnostic center, various data associated with the customer and one or more of the tests and procedures administered to the customer is provided to a remote practitioner (e.g., via a remote practitioner device) to allow the remote practitioner to confirm, evaluate and diagnose the customer's visual ability and/or eye health and/or create a vision and/or eye health report (or similar evaluation) to be provided to the customer.

In certain of these embodiments, this process may occur asynchronously. In other words, after the customer has received the vision examination and/or eye health examination, the system may deliver the customer data and customer examination data to the remote practitioner (or make such data available to the remote practitioner through a web-based service and/or software application installed on the remote practitioner device). At some later time, the remote practitioner may then review and analyze the data, diagnose and confirm various aspects of the customer's vision and eye health, and generate and/or send back customer evaluation data (e.g., vision report, eye health report, optical prescriptions, etc.), which can then be sent or made accessible to the customer (e.g., at a customer diagnostic center, at a device associated with the customer, etc.).

In certain other embodiments, assistance from remote practitioners may occur synchronously. In certain of these embodiments, when a customer requests a vision examination and/or eye health examination through a customer diagnostic center (or at some point during the examination or examination process), the system may be configured to establish a real-time connection to a remote practitioner. As a result, this allows the remote practitioner to review and evaluate the customer examination data and provide evaluations and reports to the customer in real-time or near real-time. Additionally, or as an alternative, the remote practitioner may be able to monitor and control the ophthalmic equipment and instruments and/or the administration of the tests and procedures to the customer, in a similar manner to that described above for the on-site (or remote) operator, through the real-time connection with the customer diagnostic center.

For example, in certain embodiments, some or all of the ophthalmic equipment and instruments at the customer diagnostic center may be connected to a personal computer running Windows or any other suitable operating system and having a client application installed that provides an interface to (e.g., sends commands to and receives data from) the equipment. The client application may be any suitable application capable of providing a remote interface to the ophthalmic equipment, such as the Eyelogic touchscreen-enabled Windows application available from Eyelogic Systems, Inc. In certain embodiments, the client application may store various data (e.g., in a database stored in local memory at the customer diagnostic center), including data received from the ophthalmic equipment and/or customers. In certain of these embodiments, such as where the personal computer and/or customer diagnostic center includes various recording devices (e.g., a video recorder, microphone, etc.) the client application may record and/or store the vision examination and/or eye health examination session (e.g., the interactions with the customer, tests administered to the customer, etc.).

In certain embodiments, the client application and/or personal computer may be connected to a tele-presence system, which may be any suitable system for establishing a real-time connection with, and routing or streaming various data to and from a remote agent (e.g., a remote practitioner via a remote practitioner device). For example, the client application and/or personal computer may be connected to a tele-presence client framework or endpoint, such as the VidyoDesktop software application available from Vidyo, Inc. The endpoint may connect to a tele-presence server and/or server framework, such as a VidyoRouter server available from Vidyo, Inc, via any suitable network and/or network protocol (e.g., the Internet and/or Session Initiation Protocol). In certain of these embodiments, the tele-presence server and/or server framework may be integrated with and/or run on one or more CDC servers or RPM servers included with the eye testing and evaluation system (such as CDC servers 20 and 20a-20c and/or RPM server 24 shown and described above in connection with FIGS. 1 and 2).

According to certain embodiments, the tele-presence server and/or server framework may be configured to route the examination and/or examination session to an available remote practitioner, such as via a CTS-500 Endpoint or other suitable tele-presence client framework or endpoint associated with the remote practitioner (e.g., an endpoint integrated with or connected to a remote practitioner device). As a result, data associated with the examination and/or examination session can be streamed or otherwise delivered to the remote practitioner in real-time. In certain of these embodiments, the endpoint associated with the remote practitioner may be configured to send various data back to the endpoint associated with the customer diagnostic center, thereby enabling two-way communication between the remote practitioner and the customer. For example, the remote practitioner may send back commands for controlling the ophthalmic equipment and/or the administration of the tests, audio/video data to be output to the customer (e.g., instructions, questions, guidance, etc.) and/or evaluation data pertaining to the customer's vision and/or eye health (e.g., vision and/or eye health reports, prescriptions, recommendations, referrals, etc.).

In certain other embodiments, the tele-presence system may enable real-time teleconferencing and video conferencing to be established without the need for specialized networks, endpoints, and/or other hardware (e.g., dedicated cameras, microphones, monitors, firmware, etc.). For example, the system may utilize a centralized teleconferencing infrastructure, which enables and manages conferencing between software endpoints (e.g., devices having certain software installed). In certain embodiments, this centralized conferencing architecture may be provided and managed by a separate service provided, such as the VidyoRouter service provided by Vidyo, Inc. Importantly, the use of this type of centralized architecture allows for the conferencing functions to be performed at the customer diagnostic centers via the same hardware (e.g., computer, monitor, etc.) used for controlling the ophthalmic equipment, interfacing with the customers, and/or administering the vision tests and eye examinations. In certain of these embodiments, the conferencing software that is installed and executed at the customer diagnostic centers and/or remote practitioner devices may be customized in any suitable manner, such as to display or present various data to a customer prior to, or during, a conference (e.g., customer data, prior examination data, introductory videos, logos, etc.).

According to certain embodiments, such as where a real-time conference is established between a customer and remote practitioner during the administration of a vision and/or eye health examination, the examination and conference (or a portion thereof) may be recorded and stored, such as at the centralized teleconferencing system. In certain of these embodiments, these stored recordings may be accessible to one or more individuals, such as the customer, remote practitioner, and/or other practitioners. For example, the remote practitioner may wish to replay some or all of the recorded examination session in connection with reviewing and analyzing the customer's examination data and/or providing a prescription or eye health report. As another example, the recorded examination session may be provided to another practitioner for review, such as in the case where the customer is referred to a specialist practitioner for further or follow-up testing, diagnosis and/or treatment.

As shown by the foregoing discussion, the ability for customers who are receiving vision examinations and/or eye health examinations at a customer diagnostic center to connect to and interface with remote practitioners in real-time provides a number of important benefits. One such benefit is that it enables the remote practitioners to "touch and feel" the customers, such as by interacting with and interrogating the customers, thereby allowing the remote practitioners to provide a more meaningful and accurate evaluation of the customers' vision and eye health. Another such benefit is that it allows customers to receive vision examinations and/or eye health examinations in virtually the same manner as an in-person screening or examination, while significantly reducing the time, inconvenience and expense associated with visiting a practitioner's office to obtain the in-person screening or examination.

In addition, by utilizing one or more of the systems and methods for implementing various degrees of automation and/or assistance at the customer diagnostic centers, the eye testing and evaluation system enables a great deal of flexibility and customizability. For example, certain customer diagnostic centers could be configured to provide fully-automated vision examinations and/or eye health examinations or examinations with limited on-site assistance, thereby allowing customers to obtain examinations with little or no assistance and minimizing the corresponding time and cost required. In certain embodiments, these fully-automated (or minimally assisted) vision examinations and/or eye health examinations could be in the form of limited or partial examinations (e.g., examinations having a limited set of tests and procedures that are capable of being automatically processed and evaluated by the system). In turn, some or all of these customer diagnostic centers (or others) may give customers the option of receiving a more extensive or comprehensive vision examination and/or eye health examination (e.g., at a higher cost), such as examinations that require the assistance of a remote practitioner.

Vision and Eye Health Evaluations

As mentioned above, in connection with a customer receiving a vision examination and/or eye health examination through a customer diagnostic center, the customer diagnostic center and/or eye testing and evaluation system may generate and/or provide the customer with customer evaluation data pertaining to the customer's vision and/or eye health, such as one or more reports, charts, documents, summaries, test results, recommendations, referrals, treatments, etc. In certain of these embodiments, some or all of the customer evaluation data may be automatically generated by the customer diagnostic center and/or eye testing and evaluation system, such as by applying various software and algorithms to, and otherwise processing, the data associated with administering the tests and procedures to the customer and/or other data (e.g., customer data). Alternatively, or in addition, some or all of the customer evaluation data may be received (or be based on data received) from a remote practitioner, such as in response to providing the customer examination data and customer data to the remote practitioner for review and analysis.

In certain embodiments, such as where a customer receives a vision examination through a customer diagnostic center, the customer evaluation data may include vision evaluation data, such as an optical prescription, set of optical specifications and/or an order for eyeglasses and/or contact lenses (e.g., FDA Class I, OTC medical devices). In certain of these embodiments, such as where the customer evaluation data is received (or based on data received) from a remote practitioner, the optical prescription (and/or optical specifications or order) may be signed by the remote practitioner (e.g., using an electronic signature or similar mechanism) and dated. The optical prescription may or may not indicate an expiration date and/or may indicate to the customer that the optical prescription can be filled by the optical dispenser of the customer's choice.

In certain embodiments, the vision evaluation data may include data and information pertaining to one or more parameters associated with the customer's visual acuity, such as the parameters used to determine the refractive error of the customer's eyes. For example, the vision evaluation data may include the strengths or curvatures in degrees and/or Diopters (e.g., converted from millimeters of radius of curvature into Dioptric strength power) for one or more components of visual acuity, such as (1) Sphere in Diopters (e.g., in connection with simple myopia/nearsightedness and hyperopia/farsightedness); (2) Cylinder Power in Diopters (e.g., in connection with astigmatism), (3) Axis of Cylinder in degrees from 0 to 180 (e.g., in connection with astigmatism); and/or (4) another Sphere in Diopters, such as bifocal power pertaining to additional correction needed for reading (e.g., in connection with presbyopia, typically present in individuals over 45). In certain embodiments, the vision evaluation data may include information that indicates the corrected and/or un-corrected visual acuities for the customer's eyes, which may include each eye separately, e.g. 20/40 in the left eye at distance, and/or for the two eyes together. In certain of these embodiments, the vision evaluation data may include an explanation for such visual acuities (e.g. in order for a person with 20/40 vision to see what someone with normal 20/20 vision sees at 40 feet distance, the person with 20/40 vision must be 20 feet away from the same object).

In addition to (or instead of) the optical prescription, the vision evaluation data may include a vision report that provides information concerning any specific vision or refractive disorders or conditions that were detected and/or diagnosed through the vision examination. For example, the vision report may indicate whether or not the customer has certain vision disorders or conditions, such as simple myopia; simple hyperopia; mixed compound astigmatism, hyperopic astigmatism, myopic astigmatism, and/or presbyopia. If any such vision disorders or conditions were detected and/or diagnosed, the vision report may include additional information pertaining to the disorder, such as a general description, recommended treatment, etc. In certain of these embodiments, if one or more particular types of disorders or conditions are detected, the vision report and/or vision evaluation data may include a referral for the customer to visit a practitioner in-person.

According to certain embodiments, such as where a customer receives an eye health examination through a customer diagnostic center, the customer evaluation data may include eye health evaluation data. In certain of these embodiments, the eye health evaluation data may include an eye health report, in a similar manner to the vision report described above. For example, the eye health report may include various data and information that indicates whether the customer's eyes were found to be normal, healthy and/or functioning properly. In certain of these embodiments, the eye health report may indicate whether or not the customer has certain eye disorders or conditions, such as glaucoma, corneal defects, cataracts, color blindness, etc. and may include additional information pertaining to any such disorder or condition that has been detected and/or diagnosed.

In certain embodiments, when one or more eye disorders or conditions have been detected and/or diagnosed, the eye health evaluation data may indicate whether there is a need for the customer to seek further evaluation, testing and/or treatment through an in-person consultation with an eye health practitioner (e.g., an eye surgeon or other specialist). In certain embodiments, such as where the customer examination data is provided to a remote practitioner for review, the need for further in-person evaluation may be based on determinations or recommendations received from the remote practitioner. Alternatively, or additionally, the system may be configured to automatically detect and/or flag certain examination data or results as indicating a potential need for the customer to seek further evaluation (as described in more detail below). In certain embodiments, the eye health evaluation data may include referrals for the customer to see one or more particular eye health practitioners. In certain of these embodiments, the eye health report may indicate that the referral is urgent and/or mandatory, such as in order to prevent or reduce the risk of permanent vision loss.

According to certain embodiments, the vision evaluation data and/or eye health evaluation data may include one or more recommendations for the customer pertaining to future vision examinations and/or eye health examinations. For example, the vision evaluation data and/or eye health evaluation data may indicate a recommendation for how often the customer should obtain vision examinations and/or eye health examinations (e.g., once a year, once every two years, etc.). In certain embodiments, these recommendations may be based on various customer data (e.g., the customer's age, ethnicity, sex, vision/eye health, individual and family medical history, length of time since the customer's previous examination), and/or risk profiles and similar information provided by various well-known vision and eye health organizations (e.g., the American Academy of Ophthalmology). Likewise, in certain embodiments, the urgency of other recommendations (e.g., referrals to see other practitioners) may be determined in a similar manner. In certain embodiments, the vision evaluation data and/or eye health evaluation data may also include specific diagnoses and/or indicate an actual or suspected condition of a customer's eyes (e.g., whether a customer has healthy eyes or is suspected of having an eye disease, abnormality or other condition).

While the foregoing discussion describes certain types of information that may be included in the customer evaluation data provided to customers who receive vision examinations and/or eye health examinations through the customer diagnostic centers, it should be understood that the particular types of information described are intended to be exemplary, not exhaustive, and various other types of information could easily be included and/or utilized instead of some or all of the information described above. Similarly, although the vision evaluation data and eye health evaluation data are described separately in the discussion above, it should be understood that, in certain embodiments, some or all of the data and information associated with the vision evaluation data and eye health evaluation data may be combined or integrated. For example, in certain embodiments, such as where the customer receives both a vision examination and eye health examination or where the eye health examination incorporates one or more tests associated with vision examination, the customer evaluation data may include a combined vision/eye health report having some or all of the information associated with the vision evaluation data and eye health evaluation data described above.

In certain embodiments, customers may be able to access the customer evaluation data (or a portion thereof) through the customer diagnostic centers. In certain of these embodiments, such as where the vision examination and/or eye health examination is fully automated (or only involves assistance from an on-site operator) or where a real-time connection is established with a remote practitioner, the customer evaluation data may be provided to the customer at the customer diagnostic center (e.g., displayed on one or more screens) during and/or shortly after the customer receives the vision examination and/or eye health examination. Alternatively (or in addition), the customer may be able to access the customer evaluation data by returning to the same customer diagnostic center (and/or one or more other customer diagnostic centers) at a later time. In certain embodiments, the customer may be able to print out some or all of the customer evaluation data (e.g., an optical prescription or referral) using one or more printers provided at the customer diagnostic center.

According to certain embodiments, the customer evaluation data (or a portion thereof) may be sent and/or made accessible to the customers through various other systems and devices, such as one or more personal computing devices associated with the customers. For example, the customer evaluation data may be sent via e-mail or any other suitable delivery mechanism. As another example, customers may be able to access the customer evaluation data from a wide range of computing devices, such as by logging into a web-based service or application provided by the customer diagnostic center and/or eye testing and evaluation system and/or through a software application (e.g., client application, mobile app, etc.) installed on the customers' devices. In a similar manner, the customers may be able to instruct the customer diagnostic center and/or eye testing and evaluation system to forward some or all of the customer evaluation data to various third parties and/or third party systems, such as an external practitioner, optical lens lab, or third party provider of vision and eye care products and/or services. In certain of these embodiments, the customer evaluation data may be sent to the customer and/or one or more third parties automatically or only in response to a request by the customer. In certain embodiments, the customer evaluation data may be conveyed to the customer over a telephone. For example, a customer who requests to speak with a practitioner may provide a telephone number to enable the practitioner to call the customer at a convenient time.

Data Analysis for Diagnosis and Risk Prediction

In accordance with certain embodiments, such as those illustrated and described in connection with FIGS. 1-3, the customer diagnostic centers and/or other components of the eye testing and evaluation system (e.g., CDC servers, database servers, etc.) may store and/or update a wide range of data in connection with providing vision examinations and/or eye health examinations to customers. The eye testing and evaluation system may store and/or update various customer data (e.g., background and demographical data, prior vision examination and/or eye examination results, individual and family medical history, and other characteristics and preferences) associated with the customers. Similarly, the eye testing and evaluation system may store and/or update customer examination data (e.g., customer inputs and responses, instrument measurements, tests and procedures performed, etc.), customer evaluation data (e.g., reports, prescriptions, recommendations, referrals, digital images and other imaging data, etc., generated by the system and/or received from remote practitioners) and/or other types of data associated with the vision examinations and/or eye health evaluations provided to customers through the customer diagnostic centers.

In certain embodiments, the eye testing and evaluation system may store and/or update testing analytics data associated with reviewing, analyzing and processing the customer examination data and/or customer data, such as one or more algorithms and formulas (e.g., to calculate refractive error) and/or various standards, norms, and metrics (e.g., normal or acceptable ranges for certain parameters) that may be applied to the measurements or test results and/or otherwise utilized in connection with detecting or diagnosing various disorders, defects and conditions and evaluating the customers' vision and eye health. Additionally (or alternatively), the eye testing and evaluation system may store and/or update risk prediction data pertaining to various risk factors, risk profiles, correlations and similar information that is associated with vision and eye related disorders, defects and conditions that are more likely to occur in certain groups of individuals.

In certain of these embodiments, the risk prediction data may include risk factors and the like that are based on a person's background (e.g., welders are more prone to have corneal scars that can cause irreversible loss of vision), ethnicity (e.g., Hispanic Americans are more prone by 20% to acquire glaucoma, and African Americans are 40% more prone to acquire glaucoma, as compared to Caucasian Americans), income (e.g., lower income families typically have less frequent eye exams and refractions, and less primary medical health care, and are more prone to irreversible vision caused by diabetes and hypertension), prior medical history (e.g., individuals with pre-existing hypertension, diabetes, or history of eye disease and/or disorders, eye surgeries, etc., are more prone to certain systemic eye disorders and syndromes, such as syphilis, Bell's Palsy, shingles, etc.), age (e.g., individuals over sixty are more prone to certain age related eye diseases (AREDS), such as cataracts, glaucoma, diabetic retinopahy, macular degeneration, etc.).

According to certain embodiments, some or all of this data (and various other data) may be utilized by the eye testing and evaluation system in a number of different ways. In certain embodiments, the eye testing and evaluation system may use this data to determine whether customers have a higher risk for various vision and eye related disorders, defects and/or conditions. For example, in response to receiving new or updated customer data (and/or other data) from a customer, the customer diagnostic center and/or eye testing and evaluation system may compare the customer data to the prediction data to determine whether the customer's demographics, characteristics, etc. match any risk profiles or factors in the prediction data. In certain of these embodiments, the eye testing and evaluation system may create and store an individual risk profile for new customers that includes a list of any high-risk disorders, defects, and/or conditions identified for the customer (e.g., prescreen the new customers) and/or update the individual risk profile when additional or updated customer data is received.

In turn, the individual risk profile (or similar data) could be included with the customer examination data for the customer that is sent to a remote practitioner (e.g., to assist the remote practitioner's review and evaluation) and/or used to select, modify and/or tailor tests and procedures administered to the customer and various recommendations provided to the customer. In certain of these embodiments, the eye testing and evaluation system may use the individual risk profiles and/or other data (e.g., customer data and customer evaluation data) to create and update a customized testing plan for a customer. For example, the customized testing plan may include one or more customized vision examinations and eye health examinations (e.g., specifying a particular group of tests and procedures to be administered), a recommended schedule for receiving such vision examinations and eye health examinations, recommended actions, medicines or treatments, and/or referrals to see one or more eye care practitioners in-person (e.g., on a one-time and/or periodic basis).

In certain embodiments, the eye testing and evaluation system may use some or all of the stored data described above in connection with evaluating the customer examination data and other data associated with administering vision examinations and/or eye health examinations to customers through the customer diagnostic centers. For example, the eye testing and evaluation system may process and analyze the customer examination data based on the testing analytics data, such as to automatically calculate various parameters using pre-defined formulas and/or detect and diagnose certain disorders, defects and conditions by comparing the customer examination data to one or more standards (e.g., normal or acceptable ranges or results). In certain embodiments, the system may utilize software to analyze images or other digital scanning data to diagnosis and/or risk prevention purposes. For example, images or scanning data associated with the ganglion cell layer may be analyzed by the software for detecting or preventing chronic glaucoma. In certain of these embodiments, such as where the customer examination data is sent to remote practitioners, the eye testing and evaluation system may instead (or in addition) use the testing analytics data to pre-process and package the customer examination data before providing it to the remote practitioner. For example, in connection with measuring or calculating a particular parameter (e.g., intraocular pressure) the eye testing and evaluation system may create a chart or graph that shows the parameter for the customer in relation to an acceptable range associated with the parameter. Importantly, pre-processing and packaging the customer examination data that is provided to remote practitioners makes it easier and more efficient for remote practitioners to review the data and/or confirm the results, thereby reducing the time associated with evaluating and providing reports to each customer.

In certain embodiments, the eye testing and evaluation system may use some or all of the stored data described above to track and evaluate the customers' vision and/or eye health over time. For example, when a customer receives a vision examination and/or eye health examination through a customer diagnostic center, the examination data and/or evaluation data may be compared with data for previous vision examinations, eye health examinations and other similar tests received by the customer (e.g., data associated with previous tests received through a customer diagnostic center, from an external practitioner, or a combination thereof). In certain of these embodiments, the eye testing and evaluation system may generate and/or update various charts, graphs, images, summaries, etc. using the current and previous examination and/or evaluation data, such as to show the progression of one or more parameters, defects, disorders, and/or conditions. For example, after a customer receives a vision examination, the eye testing and evaluation system may create or update a chart that illustrates the changes in the refractive error of the customer's eyes over a specified period. In certain embodiments, these charts, graphs, and/or other tracking data associated with the progression of the customer's vision and/or eye health may be included with the customer examination data that is sent to the remote practitioners in order to assist the remote practitioners in making an informed evaluation and diagnosis.

In turn, by keeping track of customers' vision and/or eye health over time, the eye testing and evaluation system can determine whether a treatment previously prescribed to the customer is working (e.g., whether there has been any improvement or change in a defect or condition being treated), and/or evaluate the outcome of a surgery, operation or procedure previously performed on the customer. Similarly, the eye testing and evaluation system may use the tracking data in connection with detecting and/or diagnosing certain disorders, defects and/or conditions and/or determining whether a customer should be referred to one or more external eye care practitioners. For example, if the eye testing and evaluation system detects that a customer's visual acuity is worsening or not improving despite the use of refractive lenses, this may be a strong indication that the customer has a medical anomaly, disorder or disease (e.g., optic nerve inflammation or infection, amblyopia, cataracts, etc.) and the system may refer the customer to an eye-care practitioner or specialist (e.g., a cataract specialist).

According to certain embodiments, the eye testing and evaluation system may use some or all of the stored data described above to tweak or modify certain existing risk factors, risk profiles, standards, correlations etc. and/or identify new risk factors. For example, the eye testing and evaluation system may analyze the customer data, customer examination data and/or customer evaluation data to search for potential correlations between various parameters (e.g., female Asian Americans have a 30% higher risk of developing cataracts). Similarly, the eye testing and evaluation system may analyze this data to confirm the accuracy of existing risk factors and correlations and/or various standards and norms (e.g., normal ranges for parameters). In turn, as customer data and examination and evaluation data is continuously collected, compiled and processed by the system, these risk factors, correlations and/or standards can be periodically updated to reflect the data.

Exemplary Method for Providing an Eye Testing and Evaluation Service

Figure 6:
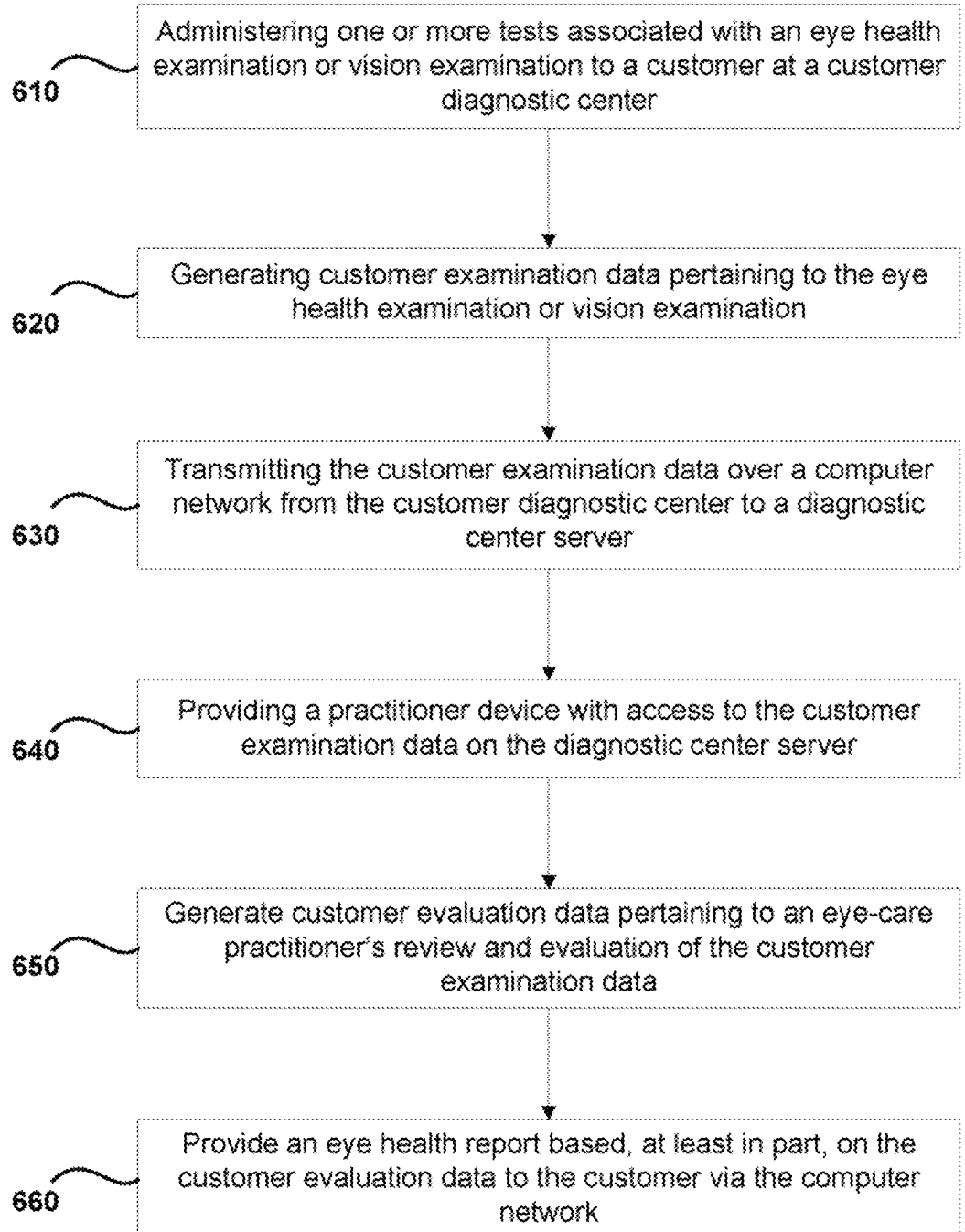
FIG. 6 is a flow chart illustrating an exemplary method for administering an eye testing and evaluation service in accordance with certain embodiments of the present invention.

FIG. 6 is a flow chart illustrating an exemplary method 600 for administering an eye testing and evaluation service in accordance with certain embodiments of the present invention. Initially, one or more tests associated with an eye health examination and/or vision examination are provided to a customer (step 610). In certain embodiments, the one or more tests may be administered at a customer diagnostic center. Next, customer examination data relating to the eye health examination and/or vision examination is generated (step 620). The customer examination data may include any data associated with the customer and any data that enables or assists a remote practitioner to evaluate the customer's eye health and visual ability, detect and diagnose certain disorders, defects and conditions and/or confirm that one or more of the tests and procedures were administered correctly. In certain embodiments, the customer examination data may include data associated with the customer (e.g., the customer's name, age, gender, race, medical history, prior test results, etc.) and data associated with one or more of the tests administered to the customer (e.g., responses, inputs and selections from the customer, instrument measurements and readings, test results, etc.). In certain embodiments, the customer examination data may include a live video stream or video recording of the eye health examination and/or vision examination that was provided to a customer.

The customer examination data is transmitted over a computer network (e.g., the Internet) from a customer diagnostic center to a diagnostic center server (step 630). The diagnostic center server may store all or a portion of the customer examination data. The diagnostic center server provides access to one or more practitioner devices to enable a practitioner device to access the customer examination data (step 640). This permits a practitioner operating a practitioner device to review the customer examination data from a location that is located remotely from the customer diagnostic center where the one or more tests are administered to the customer. In certain embodiments, a practitioner may access the customer examination data in real-time as tests are being administered to the customer. In certain embodiments, a practitioner may access the customer examination data after the tests are administered to the customer.

After or while the practitioner is reviewing the customer examination data, customer evaluation data is generated that pertains to the eye-care practitioner's review and evaluation of the customer examination data (step 650). The customer evaluation data received from the remote practitioner may include various reports, diagnoses, recommendations and other information indicating the results of the eye health and vision tests and procedures administered to the customer. In certain embodiments, the customer evaluation data may include an eye health report or may be used to generate an eye health report. The eye health report may include a summary of the customer's eye health, visual acuity, test results and procedures, diagnoses, optical prescriptions, pharmaceutical prescriptions, recommendations, treatment instructions, referrals to see other eye care professionals, and/or other data that is associated with the customer, practitioner or the customer's visit to the customer diagnostic center. The eye health report which is based, at least in part, on the customer evaluation data is then provided to the customer through the network (step 660). The eye health report may be provided to a customer in various ways. In certain embodiments, the eye health report may be presented to the customer through the diagnostic center 10. In certain embodiments, the customer may be permitted to access the eye health report using one or more computing devices associated with the customer. In certain embodiments, the customer may be permitted to download a copy of the eye health report from a website after logging in (e.g., with a username and password) to an account on the website. In certain embodiments, the eye health report may be transmitted to the customer via electronic mail.

Exemplary Methods for Providing Vision and Eye Health Examinations

Figure 7:
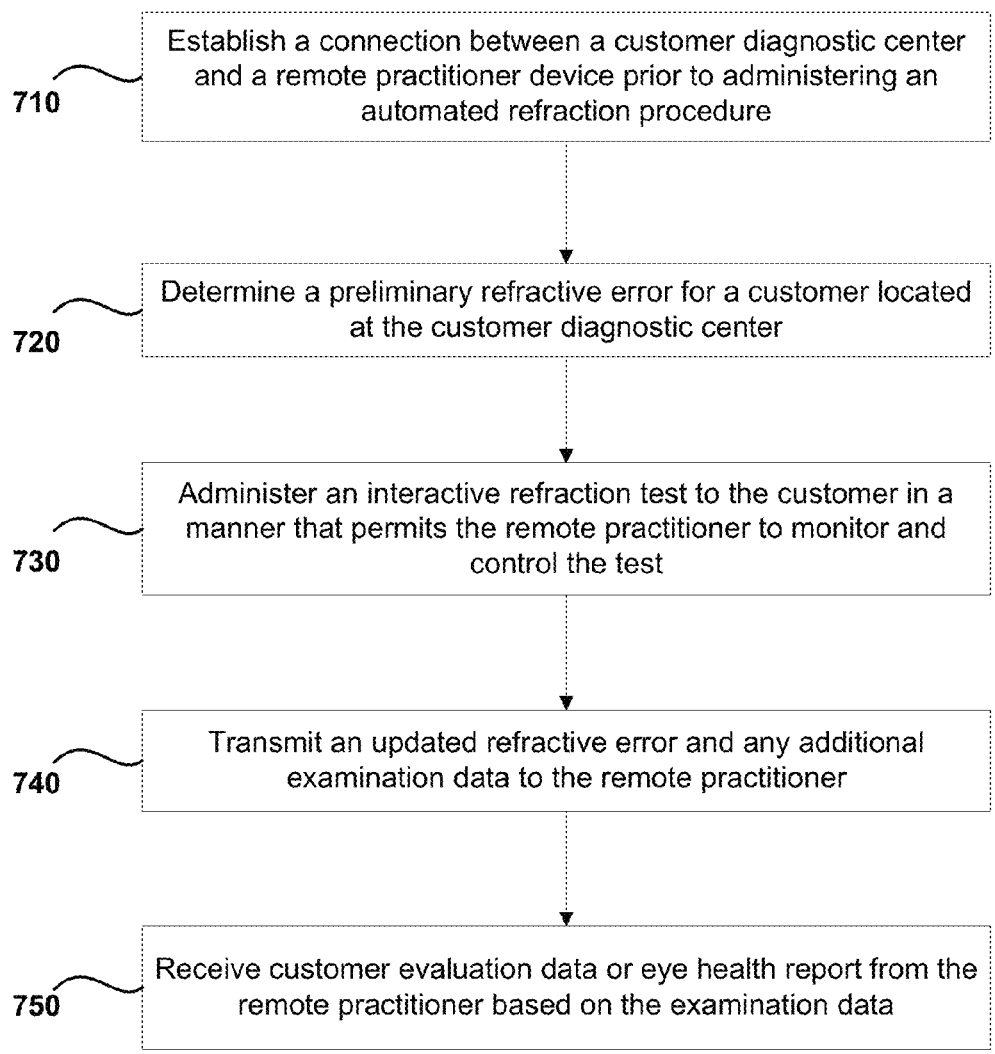
FIG. 7 is a flow chart illustrating an exemplary method for administering a synchronous vision examination in accordance with certain embodiments of the present invention.

FIG. 7 is a flow chart illustrating an exemplary method 700 for administering a synchronous vision examination in accordance with certain embodiments of the present invention. Initially, a connection is established between a customer diagnostic center 10 and a remote practitioner device 30 (step 710). In certain embodiments, a request may be transmitted to a server from the customer diagnostic center for establishing the connection and the request may be accepted by the remote practitioner device 30. A remote practitioner associated with the remote practitioner device 30 may be selected by the server or an individual at the customer diagnostic center 10 and the remote practitioner may choose whether or not to accept the request. In certain embodiments, the connection may be established through the server (e.g., customer diagnostic center server 20, remote practitioner management server 24 or other server) or made directly between the customer diagnostic center 10 and the remote practitioner device 30. In certain embodiments, the connection may provide a live audio/video stream to both the remote practitioner device 30 and the customer diagnostic center 10 in order to facilitate communication between a remote practitioner who is operating the remote practitioner device 30 and a customer and/or on-site personnel located at the customer diagnostic center 10. Any data transmitted via the connection may be encrypted for security purposes.

Next, a preliminary refractive error is determined for the customer located at the customer diagnostic center 10 (step 720). The preliminary refractive error may be determined by analyzing prior prescriptions, analyzing data associated with prior vision examinations, retrieving customer data that is stored in a database or a tangible record, utilizing a lensometer 144, or by other means.

After a preliminary refractive error is determined for the customer, an interactive refraction test may be administered to the customer in a manner that permits the remote practitioner to monitor and control the vision examination (step 730). In certain embodiments, the remote practitioner may be presented with an interface on the remote practitioner device 30 that permits the practitioner to control the equipment (e.g., turn the equipment on/off, move the equipment, take measurements, etc.). For example, by selecting interface elements (e.g., buttons, links or on-screen controls) on the interfaces, the practitioner may cause the remote practitioner device 30 to transmit commands to the equipment controller 130 located at the customer diagnostic center 10, thus permitting the practitioner to operate and manipulate the equipment. The remote practitioner may be permitted to control any equipment that is relevant to providing a vision examination including, but not limited to, an auto phoropter 141, lens houser 142, auto-refractor 143, lensometer 144 and eye chart 145 (and any projector associated with an eye chart). In certain embodiments, the remote practitioner may not be able to directly control the equipment. Rather, personnel at the diagnostic center 10 may control the equipment and the remote practitioner may provide instructions to the personnel via the established connection.

After or while the vision examination is administered, examination data associated with the vision examination (including examination data that indicates an updated refractive error for the customer) may be transmitted to the remote practitioner device 30 for review by the remote practitioner (step 740). In response, the customer may receive evaluation data and/or an eye health report from the remote practitioner (step 750). In certain embodiments, the evaluation data and/or an eye health report may be transmitted to the customer diagnostic center 10 from the remote practitioner device 30 while the customer is present at the customer diagnostic center 10. In certain embodiments, the evaluation data and/or an eye health report may be transmitted to the customer after the customer leaves the customer diagnostic center 10 (e.g., via e-mail, traditional mail service, or through a website).

Figure 8:
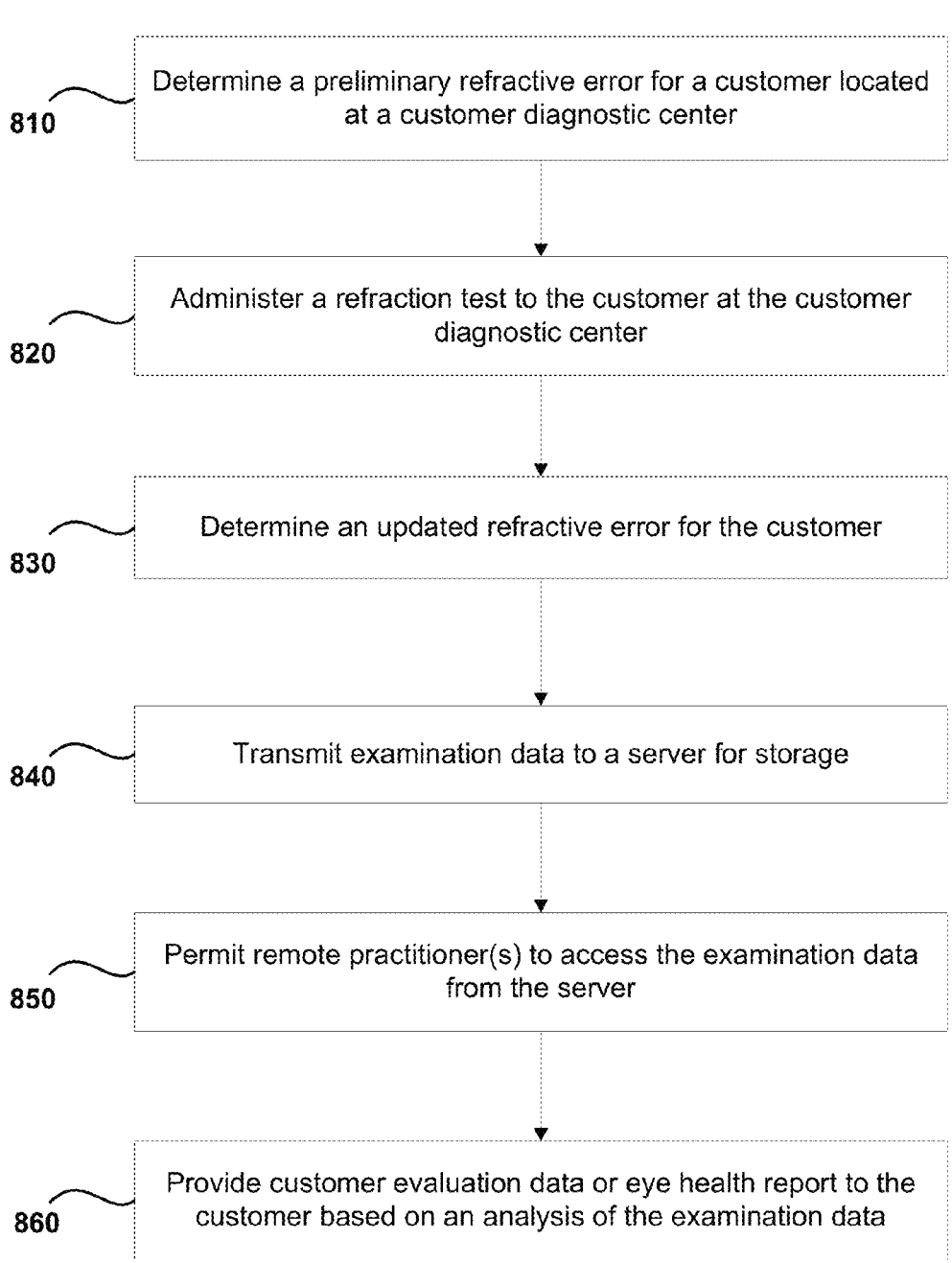
FIG. 8 is a flow chart illustrating an exemplary method for administering an asynchronous vision examination in accordance with certain embodiments of the present invention.

FIG. 8 is a flow chart illustrating an exemplary method 800 for administering an asynchronous vision examination in accordance with certain embodiments of the present invention. A preliminary refractive error may initially be determined for a customer located at a customer diagnostic center 10 (step 810). The preliminary refractive error may be determined in the same ways discussed above. In certain embodiments, this step may be performed by technicians, operators, or other personnel located at the customer diagnostic center 10. In certain embodiments, this step may be performed by the customer (e.g., by permitting the customer to specify preliminary refractive error results from prior examinations). Next, a refraction test may be administered to the customer at the customer diagnostic center 10 (step 820) and an updated refractive error may be determined for the customer (step 830). Once again, these steps may be performed by technicians, operators, or other personnel located at the customer diagnostic center 10. In certain embodiments, the step of determining an updated refractive error may be performed at a subsequent time by a remote practitioner after reviewing the examination data associated with the vision examination.

After the refraction test is administered to the customer (and possibly after an updated refractive error has been determined), examination data associated with the vision examination is transmitted to a server for storage (step 840). The server may represent a customer diagnostic center server 20, remote practitioner management server 24 or other server. In certain embodiments, the vision examination system may be provided, at least in part, by a cloud-based service and the server may be associated with the cloud-based service. In certain embodiments, the stored examination data may be associated with a particular remote practitioner (e.g., which may be selected by a round robin process or who may be a practitioner who has serviced the customer in the past). One or more remote practitioners may be provided with access to the stored examination data located on the server (step 850). In certain embodiments, the remote practitioners may receive and accept a request for providing the asynchronous vision examination for the customer. The remote practitioners may be selected by an individual at the customer diagnostic center or by the server. In certain embodiments, the remote practitioner may enter login credentials (e.g., username and password) to access the stored examination data associated with the customer. After reviewing the examination data, the remote practitioner may provide evaluation data and/or eye health report to the customer (step 860). Once again, the evaluation data and/or an eye health report may be transmitted to the customer after the customer leaves the customer diagnostic center 10.

Figure 9:
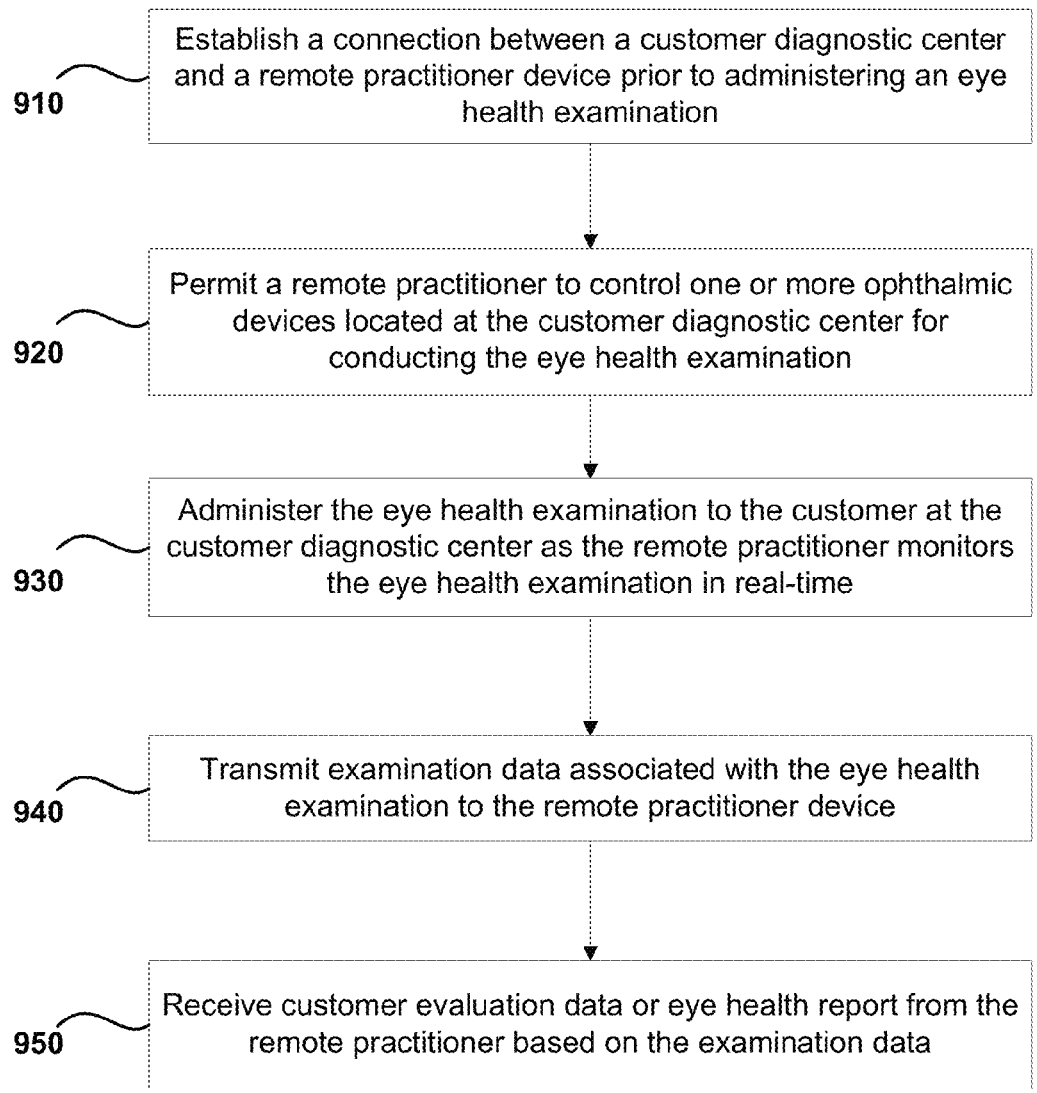
FIG. 9 is a flow chart illustrating an exemplary method for administering a synchronous eye health examination in accordance with certain embodiments of the present invention.

FIG. 9 is a flow chart illustrating an exemplary method 900 for administering a synchronous eye health examination in accordance with certain embodiments of the present invention. A connection may be established between a customer diagnostic center 10 and a remote practitioner device 30 prior to administering an eye health examination (step 910). In certain embodiments, a request may be transmitted to a server from the customer diagnostic center for establishing the connection and the request may be accepted by the remote practitioner device 30. A remote practitioner associated with the remote practitioner device 30 may be selected by the server or an individual at the customer diagnostic center 10 and the remote practitioner may choose whether or not to accept the request. In certain embodiments, the connection may be established through a server (e.g., customer diagnostic center server 20, remote practitioner management server 24 or other server) or established directly between the customer diagnostic center 10 and the remote practitioner device 30. Once again, the connection may provide a live audio/video stream to both the remote practitioner device 30 and the customer diagnostic center 10 in order to facilitate communication between a remote practitioner who is operating the remote practitioner device 30 and a customer and/or on-site personnel located at the customer diagnostic center 10. Any data transmitted via the connection may be encrypted for security purposes.

A remote practitioner may be permitted to control one or more ophthalmic devices located at the customer diagnostic center 10 for conducting the eye health examination (step 920). As explained above, the remote practitioner may be presented with an interface on the remote practitioner device 30 that permits the practitioner to control and manipulate the equipment by selecting interface elements or in other ways. The remote practitioner may be permitted to control any equipment that is relevant to providing an eye health examination including, but not limited to, a digital imager 151, bio-microscope 152, retinal camera 153, tonometer 154 and visual field instruments 155. The remote practitioner may then administer the eye health examination to the customer located at the customer diagnostic center 10 as the remote practitioner monitors the eye health examination in real-time (step 930).

After or while the eye health examination is administered to the customer, examination data associated with the eye health examination may be transmitted to the remote practitioner device 30 (step 940). In certain embodiments, the examination data may initially be transmitted to a server (e.g., customer diagnostic center server 20, remote practitioner management server 24 or other server) which may then provide the examination data to the practitioner device 30 or make the examination data available to the practitioner device 30. After the remote practitioner has reviewed the examination data, the customer may then receive evaluation data and/or eye health report from the remote practitioner (step 950). As mentioned above, the evaluation data and/or eye health report may be provided to the customer while the customer is at the customer diagnostic center 10 or afterwards by other means.

Figure 10:
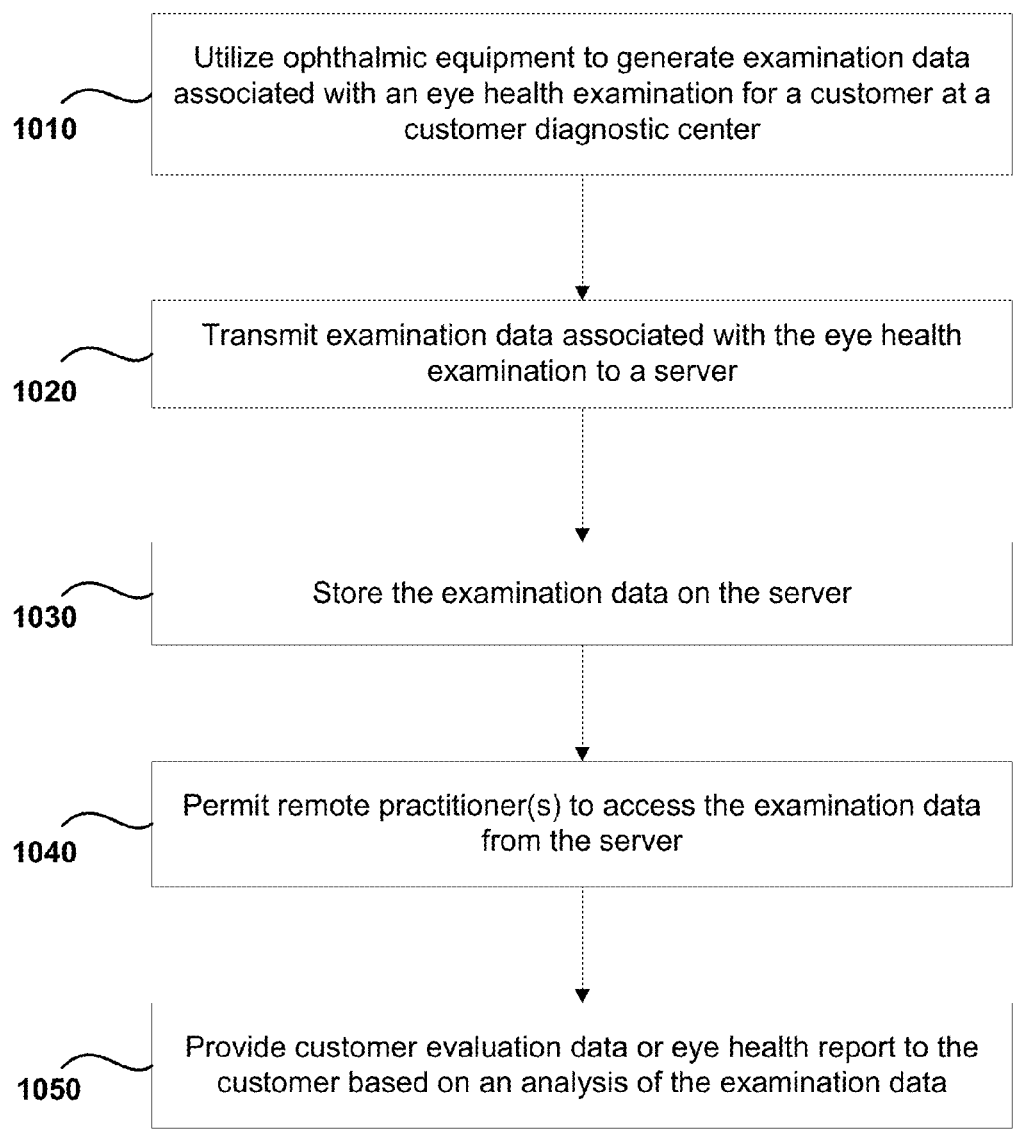
FIG. 10 is a flow chart illustrating an exemplary method for administering an asynchronous eye health examination in accordance with certain embodiments of the present invention.

FIG. 10 is a flow chart illustrating an exemplary method 1000 for administering an asynchronous eye health examination in accordance with certain embodiments of the present invention. Initially, ophthalmic equipment is utilized to generate examination data associated with an eye health examination for a customer at a customer diagnostic center (step 1010). The examination data may include data generated by ophthalmic equipment or any other data associated with the eye health examination. This step may be performed by technicians, operators, or other personnel located at the customer diagnostic center 10. After or while the examination data is generated, the examination data may be transmitted to a server (step 1020) and stored on the server (step 1030). As mentioned above, the server may represent a customer diagnostic center server 20, remote practitioner management server 24, server associated with a cloud-based service or other server. In certain embodiments, the stored examination data may be associated with one or more remote practitioners. For example, a remote practitioner may be randomly selected to review the examination data (e.g., by selecting the practitioner using a round robin process or in other ways) or may be selected to review the examination data because the practitioner previously serviced the customer in the past (e.g., previously administered a vision or eye health examination to the customer).

One or more remote practitioners may be provided with access to the stored examination data located on the server (step 1040). In certain embodiments, the remote practitioners may receive and accept a request for providing the examination for the customer. The remote practitioners may be selected by an individual at the customer diagnostic center or by the server. In certain embodiments, the remote practitioner may enter login credentials (e.g., username and password) to access the stored examination data associated with the customer. After reviewing the examination data, the remote practitioner may provide evaluation data and/or eye health report to the customer (step 1050). As mentioned above, the evaluation data and/or an eye health report may be provided to the customer while the customer is at the customer diagnostic center 10 or afterwards by other means.

It should be recognized that the above methods are merely meant demonstrate how vision and eye health examinations can be administered to customers and are not meant to be limiting. Numerous variations can be made to the methods without departing from the scope of the present invention.

Extended Services and Functionality

In certain embodiments, customers may be able to view, compare, order and/or purchase various vision and/or eye care related products and services through the customer diagnostic centers and/or the eye testing and evaluation system. For example, the customer diagnostic centers and/or the eye testing and evaluation system may store and/or access various information associated with products (e.g., eyeglasses, contact lenses, etc.) that are offered by one or more third parties. As a result, customers may be able access, view and/or browse through these products at the customer diagnostic centers (e.g., through a display screen included with the customer interface). Customers may also, or instead, be able to access the products from other devices (e.g., a computing device associated with the customer), such as through a web-based service or client application installed on the customer's device.

In certain embodiments, the customer diagnostic centers and/or the eye testing and evaluation system may display a virtual representation or simulation of the customer wearing or using a particular product in order to illustrate how certain products would look on the customer. For example, the customer may be able to view a virtual representation of his or her face and/or head, and select one or more eyeglasses to be shown with the virtual representation. In certain of these embodiments, the virtual representation of the customer may be based on data obtained through one or more tests associated with the vision examinations and/or eye health examinations (e.g., via digital imaging devices, video cameras, etc.).

According to certain embodiments, the customer diagnostic centers and/or the eye testing and evaluation system may be configured to recommend one or more vision and/or eye care related products and services to the customers. For example, the eye testing and evaluation system may select one or more products to recommend to a customer based on various data associated with the customer, such as customer data (e.g., income, sex, age, prior products purchased, etc.) and/or customer examination and evaluation data (e.g., refractive error, optical specifications, astigmatism, etc.). Similarly, the eye testing and evaluation system may determine product recommendations for a customer based on data associated with various other customers, such as by identifying products purchased by customers with similar characteristics, backgrounds, disorders, etc. In certain other embodiments, the product recommendations may be based on a "preferred" status associated with one or more third party vendors (e.g., vendors who pay a fee to emphasize their products and services).

In certain embodiments, after a customer has browsed through and selected one or more products and services, the customer may be able to order and/or purchase the selected products and services through the customer diagnostic center. In certain of these embodiments, the customer diagnostic center and/or eye testing and evaluation system may forward various data to the third party associated with the purchased products and services, such as order data, customer data, and/or customer evaluation data (e.g., optical specifications).

In certain embodiments, various advertisements and/or promotional materials (e.g., coupons, offers, discounts, etc.) may be presented or provided to customers through the customer diagnostic centers. In certain of these embodiments, for example, advertisements and promotions may be displayed to customers (e.g., through one or more displays included with the customer interface) before, during, and/or after the customer receives a vision examination and/or eye health examination through the customer diagnostic center. In certain embodiments, the advertising and promotional materials may include materials that are associated with various vision and eye care related products and services, and/or may include materials for a wide range of other consumer products and services. In certain embodiments, such as where the customer diagnostic center includes a printing device, the customers may be able to print out a hard copy of one or more promotions, such as coupons. Alternatively, or in addition, customers may be able to select an option to forward the advertisement or promotion to themselves (e.g., via e-mail or text).

Importantly, the incorporation of advertising and promotional materials and other similar services (e.g., allowing vendors to pay for preferred status) provides certain benefits to customers. One such benefit is that, given the revenue generated through such mechanisms, customers may be able to receive vision examinations and/or eye health examination at a significantly reduced cost, or may even be able to receive certain services at no charge, thereby encouraging customers to receive such examinations on a regular basis.

In certain embodiments, the eye testing and evaluation system may be configured to send various notifications and messages to customers (e.g., through email, text, and/or via one or more computing devices associated with the customers). For example, in certain embodiments, the eye testing and evaluation system may send a message to a customer to remind the customer that it is time to receive a vision examination and/or eye health examination, or to remind the customer about an upcoming appointment with an external practitioner (e.g., in connection with a previous referral for in-person evaluation). Similarly, the eye testing and evaluation system may send messages to a customer requesting confirmation that the customer has made an appointment with and/or visited an external practitioner (e.g., in the case where a referral for urgent follow-up testing was provided to the customer).

It is understood that the various systems, devices, and methods described in connection with the foregoing figures are exemplary, and any other suitable systems, devices or methods may be used. The foregoing is merely illustrative of the principles of this invention and various modifications can be made by those skilled in the art without departing from the scope and spirit of the invention. As an example, although certain embodiments of the eye testing and evaluation system have been described in connection with a particular number of customer diagnostic centers and/or remote practitioner devices having certain formats or types, the platform may include any number, format and type of customer diagnostic centers and/or remote practitioner devices. As another example, while the customer diagnostic centers have been described as having certain exemplary ophthalmic equipment and instruments, the customer diagnostic centers may utilize virtually any suitable type of such devices and instruments. One skilled in the art will appreciate that the present invention can be practiced in other than the described embodiments, which are presented for purposes of illustration and not limitation.

What is claimed is:

1. A system for providing eye health and vision examinations, comprising:
   a plurality of diagnostic centers, each of the diagnostic centers including ophthalmic equipment comprising a set of instruments that are utilized in administering eye examinations and being coupled to an equipment controller that is configured to receive instructions for controlling the ophthalmic equipment, wherein the diagnostic centers are configured to:
      transmit requests over a network to select eye-care practitioners to administer the eye examinations in real-time for customers located at the diagnostic centers;
      receive instructions over the network to permit the eye-care practitioners to control operation of the ophthalmic equipment at the diagnostic centers from a remote location in order to administer one or more tests pertaining to the eye examinations; and
      generate customer examination data pertaining to the one or more tests administered using the ophthalmic equipment;
   a plurality of practitioner devices associated with the eye-care practitioners, wherein the practitioner devices are configured to:
      receive at least a portion of the customer examination data in response to accepting one or more of the requests associated with administering the eye examinations;
      display the received customer examination data; and
      generate customer evaluation data associated with the one or more accepted requests;
   at least one server configured to:
      permit the eye-care practitioners to login to a web-based platform to administer the eye examinations to the customers over the network in real-time;
      track availability data associated with the eye-care practitioners, the availability data indicating a set of eye-care practitioners who are currently logged into the web-based platform and whether each such eye-care practitioner is currently engaged in providing a real-time eye examination through the web-based platform;
      in response to receiving the requests from the diagnostic centers, select a subset of eye-care practitioners to administer the eye examinations based, at least in part, on analyzing the availability data to identify one or more eye-care practitioners who are logged into the web-based platform and not currently providing real-time eye examinations;
      administer the one or more tests to the customers during the eye examinations conducted at the diagnostic centers utilizing the ophthalmic equipment, the eye examinations including objective portions that utilize the ophthalmic equipment to derive objective measurements pertaining to the one or more tests and subjective portions that utilize an audio response system that is configured to present questions to and receive responses from the customers pertaining to the one or more tests, wherein the subjective portions of the eye examinations are administered using an iterative process that includes:
- selecting questions to present to the customers based on both the objective measurements derived during the objective portions of the eye examinations and the responses that are received from the customers via the audio response system;
- based on the responses received from the customers via the audio response system, automatically adjusting the ophthalmic equipment utilized in administering the subjective portion of the eye examination; and
- determining that the iterative process should be concluded in response to detecting that a particular combination of the responses received from the customers satisfy one or more conditions indicating that sufficient data has been collected for the subjective portions of the eye examinations;

receive the customer examination data from the diagnostic centers;

transmit the customer examination data to the practitioner devices associated with the selected eye-care practitioners; and receive customer evaluation data from the practitioner devices associated with the selected eye-care practitioners;

wherein eye health reports based, at least in part, on the selected eye-care practitioners' review and evaluation of the customer examination data are provided to the customers.

2. The system of claim 1, wherein the at least one server is integrated with one or more of the plurality of diagnostic centers.

3. The system of claim 1, wherein the requests include requests for synchronous vision examinations, and the at least one server is further configured to:
- establish real-time connections between the practitioner devices associated with the selected eye-care practitioners and the diagnostic centers to permit communications between the customers and the selected eye-care practitioners during the synchronous vision examinations;
- transmit preliminary refractive error information stored on the at least one server to the diagnostic centers;
- permit the practitioner devices associated with the selected eye-care practitioners to remotely administer interactive refraction tests over the network via the real-time connections, wherein the instructions received by the diagnostic centers over the network are utilized to control the ophthalmic equipment while administering the interactive refraction tests; and
- receive updated refractive error information based on the interactive refraction tests from the practitioner devices associated with the selected eye-care practitioners, wherein the updated refractive error information is included in the eye health reports provided to the customers.

4. The system of claim 1, wherein the requests further include requests for asynchronous vision examinations, and the at least one server is further configured to:
- transmit preliminary refractive error information stored on the at least one server to the diagnostic centers for use during the asynchronous vision examinations;
- store customer examination data pertaining to refraction tests that are administered at the diagnostic centers on the at least one server;
- transmit the customer examination data pertaining to the refraction tests to the practitioner devices associated with the selected eye-care practitioners after the refraction tests are administered at the diagnostic centers; and
- receive updated refractive error information from the practitioner devices associated with the selected eye-care practitioners, wherein the eye health reports include the updated refractive error information.

5. The system of claim 1, wherein the requests include requests pertaining to synchronous eye health examinations, and the at least one server is further configured to:
- establish real-time connections between the practitioner devices associated with the selected eye-care practitioners and the diagnostic centers to permit communications between the customers and the selected eye-care practitioners during the synchronous eye health examinations;
- permit the practitioner devices associated with the selected eye-care practitioners to remotely administer one or more tests associated with the synchronous eye health examinations over the network via the real-time connections, wherein the instructions received by the diagnostic centers over the network are utilized to control the ophthalmic equipment during the synchronous eye health examinations; and
- receive customer evaluation data associated with the one or more tests from the practitioner devices associated with the selected eye-care practitioners while the synchronous eye health examinations are being administered;
- wherein the eye health reports provided to the customers includes at least a portion of the customer evaluation data associated with the one or more tests.

6. The system of claim 1, wherein the requests further include requests pertaining to asynchronous eye health examinations, and the at least one server is further configured to:
- receive customer examination data generated by the ophthalmic equipment at the diagnostic centers which pertains to the asynchronous eye health examinations; and
- store the customer examination data on the at least one server, wherein the selected eye-care practitioners are provided access to the customer examination data after the asynchronous eye health examinations are administered;
- wherein the eye health report received at the diagnostic center includes the selected eye-care practitioner's assessment of the customer examination data pertaining to the asynchronous eye health examination.

7. The system of claim 1, wherein the ophthalmic equipment comprises eye health equipment that enables customers to receive comprehensive eye health examinations at the customer diagnostic centers, the eye health equipment including at least one tonometer and digital imager.

8. The system of claim 1, wherein the ophthalmic equipment comprises vision screening equipment that enables customers to receive vision examinations at the customer diagnostic centers, the vision screening equipment including at least one refractor.

9. The system of claim 1, wherein the at least one server is further configured to generate aggregate result data based on an analysis of stored customer examination data for the customers.

10. The system of claim 9, wherein the aggregate result data identifies one or more risk factors pertaining to groups of individuals with a higher risk of having a particular eye health or vision disorder.

11. The system of claim 1, wherein the at least one server selects the eye-care practitioners, at least in part, by analyzing the prior customer data and identifying eye-care practitioners who were previously utilized by the customers for one or more prior eye examinations.

12. The system of claim 1, wherein the at least one server selects the eye-care practitioners, at least in part, by utilizing the scheduling data to determine whether the eye-care practitioners are currently available.

13. A server for providing services related to eye health and vision examinations, wherein the server is configured to:
   permit eye-care practitioners to login to a web-based platform to administer eye examinations to customers over a network in real-time;
   track availability data associated with the eye-care practitioners, the availability data indicating a set of eye-care practitioners who are currently logged into the web-based platform and whether each such eye-care practitioner is currently engaged in providing a real-time eye examination through the web-based platform;
   receive a request over a network from a diagnostic center to select an eye-care practitioner to administer an eye examination to a customer,
   wherein the diagnostic center includes ophthalmic equipment comprising a set of instruments that are utilized in administering the eye examination and being coupled to an equipment controller that is configured to receive instructions for controlling the ophthalmic equipment;
   in response to receiving the request, select the eye-care practitioner to administer the eye examination based, at least in part, on analyzing the availability data to identify a subset of eye-care practitioners who are logged into the web-based platform and not currently providing real-time eye examinations;
   administer one or more tests to the customer during the eye examination conducted at the diagnostic center utilizing the ophthalmic equipment, the eye examination including an objective portion that utilizes the ophthalmic equipment to derive objective measurements pertaining to the one or more tests and a subjective portion that utilizes an audio response system that is configured to present questions to and receive responses from the customer pertaining to the one or more tests, wherein the subjective portion of the eye examination is administered using an iterative process that includes:
      selecting questions to present to the customer based on both the objective measurements derived during the objective portion of the eye examination and the responses that are received from the customer via the audio response system;
      based on the responses received from the customer via the audio response system, automatically adjusting ophthalmic equipment utilized in administering the subjective portion of the eye examination; and
      determining that the iterative process should be concluded in response to detecting that a particular combination of the responses received from the customer satisfies one or more conditions indicating that sufficient data has been collected for the subjective portion of the eye examination;
   receive customer examination data generated by the ophthalmic equipment at the diagnostic center while administering one or more tests pertaining to the eye examination;
   transmit at least a portion of the customer examination data pertaining to the one or more tests to a practitioner device associated with the selected eye-care practitioner;
   receive customer evaluation data from the practitioner device associated with the selected eye-care practitioner;
   wherein an eye health report based, at least in part, on the selected eye-care practitioner's review and evaluation of the customer examination data is provided to the customer.

14. The server of claim 13, wherein the at least one server is integrated with the diagnostic center.

15. The server of claim 13, wherein the request pertains to a synchronous vision examination, and the server is further configured to:
   establish a real-time connection between the practitioner device associated with the selected eye-care practitioner and the diagnostic center to permit communications between the customer and the selected eye-care practitioner during the synchronous vision examinations;
   transmit preliminary refractive error information stored on the server to the diagnostic center;
   permit the practitioner device associated with the selected eye-care practitioner to remotely administer an interactive refraction test over the network via the real-time connection, wherein instructions are transmitted to the diagnostic center over the network to control the ophthalmic equipment while administering the interactive refraction test; and
   receive updated refractive error information based on the interactive refraction test from the practitioner device associated with the selected eye-care practitioner, wherein the updated refractive error information is included in the eye health report provided to the customer.

16. The server of claim 13, wherein a second request pertaining to an asynchronous vision examination is received by the server, and the server is further configured to:
   transmit preliminary refractive error information stored on the server to the diagnostic center for use during the asynchronous vision examination;
   store customer examination data pertaining to a refraction test that is administered at the diagnostic center on the at least one server;
   provide access to the customer examination data pertaining to the refraction test to the practitioner device associated with the selected eye-care practitioner after the refraction test is administered at the diagnostic center; and
   receive updated refractive error information from the practitioner device associated with the selected eye-care practitioner, wherein the eye health report provided to the customer includes the updated refractive error information.

17. The server of claim 13, wherein the request pertains to a synchronous eye health examination, and the server is further configured to:
   establish a real-time connection between the practitioner device associated with the selected eye-care practitioner and the diagnostic center to permit communications between the customer and the selected eye-care practitioner during the synchronous eye health examinations;

permit the practitioner device associated with the selected eye-care practitioner to remotely administer one or more tests associated with the synchronous eye health examination over the network via the real-time connection, wherein instructions received by the diagnostic center over the network are utilized to control the ophthalmic equipment during the synchronous eye health examination; and receive customer evaluation data associated with the one or more tests from the practitioner device associated with the selected eye-care practitioner while the synchronous eye health examination is being administered, wherein the eye health report provided to the customer includes at least a portion of the customer evaluation data associated with the one or more tests.

18. The server of claim 13, wherein a second request pertaining to an asynchronous eye health examination is received by the server, and the server is further configured to:

receive customer examination data generated by the ophthalmic equipment at the diagnostic center which pertains to the asynchronous eye health examination; and store the customer examination data on the server, wherein the selected eye-care practitioner is provided access to the customer examination data after one or more tests associated with the asynchronous eye health examination are administered;

wherein the eye health report provided to the customer includes the selected eye-care practitioner's assessment of the customer examination data pertaining to the asynchronous eye health examination.

19. The system of claim 1, wherein selecting the eye-care practitioners to administer the eye examinations further includes:

tracking workload data for the eye-care practitioners through the system, the workload data at least indicating how many customers are currently allocated to each eye-care practitioner;

prioritizing a manner in which customers are assigned to eye-care practitioners based, at least in part, on the workload data; and selecting the eye-care practitioners to administer the eye examinations based, at least in part, on the workload data.

20. The system of claim 19, wherein the tracked workload data further indicates when customer examination data was last allocated to each eye-care practitioner and prioritizing an assignment of customers to the eye-care practitioners includes keeping a list of the eye-care practitioners that is ordered based, at least in part, on an amount of time that has lapsed since customer examination data was allocated to each of the eye-care practitioners.

21. The system of claim 1, wherein the system is further configured to provide asynchronous eye examinations that are not administered over the network in real-time, and conducting the asynchronous eye examinations includes:

saving the customer examination data to a web-based platform to permit subsequent access to the customer examination data at a later point in time by the eye-care practitioners;

associating the customer examination data for each customer with one or more of the eye-care practitioners;

after the customer examination data is saved to the web-based platform, receiving login requests from the eye-care practitioners; and providing the eye-care practitioners with access to the customer examination data after the eye-care practitioners have logged into the web-based platform.

22. The system of claim 1, wherein the system is further configured to:

analyze the customer examination data for a plurality of customers in order to generate testing analytics data;

pre-process the customer examination data before presentation to the eye-care practitioners using the testing analytics data, wherein pre-processing the customer examination data includes creating charts or graphs that show parameters for the customers in relation to acceptable ranges associated with the parameters; and present the pre-processed customer examination data to the eye-care practitioners to permit the eye-care practitioners to easily review and confirm results associated with the customer examination data.

23. The server of claim 13, wherein the server is further configured to:

receive login requests over the network from the eye-care practitioners to access the web-based platform; and analyze the availability data to identify the subset of eye-care practitioners who are logged into the web-based platform and who are not currently providing real-time eye examinations; and select the eye-care practitioner to administer the eye examination from the identified subset.

24. The server of claim 13, wherein the server is further configured to:

analyze customer examination data for a plurality of customers in order to generate testing analytics data;

pre-process the customer examination data before presentation to the eye-care practitioners using the testing analytics data, wherein pre-processing the customer examination data includes creating charts or graphs that show parameters for the customer in relation to acceptable ranges associated with the parameters; and present the pre-processed customer examination data to the eye-care practitioner to permit the eye-care practitioner to easily review and confirm results associated with the customer examination data.

25. A server for providing eye health and vision examinations, wherein the server is configured to:

provide a web-based platform that permits asynchronous eye examinations to be conducted over a network, wherein the asynchronous eye examinations are administered at a diagnostic center that includes ophthalmic equipment comprising a set of instruments that are utilized in administering the eye examinations and being coupled to an equipment controller that is configured to receive instructions for controlling the ophthalmic equipment;

administer one or more tests to a customer during an eye examination conducted at the diagnostic center, the eye examination including an objective portion that utilizes the ophthalmic equipment to derive objective measurements pertaining to the one or more tests and a subjective portion that utilizes an audio response system that is configured to present questions to and receive responses from the customer pertaining to the one or more tests, wherein the subjective portion of the eye examination is administered using an iterative process that includes:

selecting questions to present to the customer based on both the objective measurements derived during the objective portion of the eye examination and the responses that are received from the customer via the audio response system;

based on the responses received from the customer via the audio response system, automatically adjusting ophthalmic equipment utilized in administering the subjective portion of the eye examination; and determining that the iterative process should be concluded in response to detecting that a particular combination of the responses received from the customer satisfies one or more conditions indicating that sufficient data has been collected for the subjective portion of the eye examination;

store customer examination data pertaining to the one or more tests that are administered to a customer during the eye examination provided at the diagnostic center to permit the customer examination data to be accessed by eye-care practitioners after the customer has completed the one or more tests;

select an eye-care practitioner to evaluate the stored customer examination data;

transmit a request to the selected eye-care practitioner to evaluate the stored customer examination data;

in response to the eye-care practitioner accepting the request, associate the stored customer examination data with the eye-care practitioner;

provide the selected eye-care practitioner with access to the stored customer examination through the web-based platform; and receive customer evaluation data from a practitioner device associated with the selected eye-care practitioner;

wherein an eye health report based, at least in part, on the selected eye-care practitioner's review and evaluation of the customer examination data is provided to the customer.

26. The server of claim 25, wherein the server is further configured to:

track workload data for the eye-care practitioners associated with the web-based platform, the workload data at least indicating how many customers are currently allocated to each eye-care practitioner;

prioritize a manner in which customers are assigned to eye-care practitioners based, at least in part, on the workload data; and select the eye-care practitioner based, at least in part, on the workload data.

27. The server of claim 26, wherein the tracked workload data further indicates when customer examination data was last allocated to each eye-care practitioner and prioritizing an assignment of customers to the eye-care practitioners includes keeping a list of the eye-care practitioners that is ordered based, at least in part, on an amount of time that has lapsed since customer examination data was allocated to each of the eye-care practitioners.

28. The server of claim 25, wherein the server is further configured to:

analyze customer examination data for a plurality of customers in order to generate testing analytics data;

pre-process the customer examination data before presentation to the eye-care practitioner using the testing analytics data, wherein pre-processing the customer examination data includes creating charts or graphs that show at least one parameter for the customer in relation to acceptable ranges associated with the parameter; and present the pre-processed customer examination data to the selected eye-care practitioner to permit the selected eye-care practitioner to easily review and confirm results associated with the customer examination data.

29. The server of claim 25, wherein the customer examination data is generated and stored on the server at a point in time when the eye-care practitioner is not logged into the web-based platform and the customer examination data is made available to the eye-care practitioner at a later point in time after the eye-care practitioner has accepted the request and has logged into the web-based platform.

30. The system of claim 1, wherein the questions presented to the customers are associated with a set of powered lenses controlled by the ophthalmic equipment utilized in administering the subjective portion of the eye examinations, and automatically adjusting the ophthalmic equipment comprises automatically causing the ophthalmic equipment to switch the powered lenses with another set of lenses having a different power based on the customers' responses received via the audio response system.

31. The system of claim 1, wherein the questions are retrieved from a predefined set of stored questions and the audio response system selects the questions to present to the customers based on the customers' responses received via the audio response system.

32. The system of claim 1, wherein the responses received via the audio response system are utilized to automatically adjust the ophthalmic equipment while administering subjective portions of both vision examinations and eye health examinations.

* * * * *